(12) United States Patent
Dannenmaier et al.

(10) Patent No.: US 8,206,580 B2
(45) Date of Patent: Jun. 26, 2012

(54) INTEGRATED BLOOD TREATMENT MODULE

(75) Inventors: Jürgen Dannenmaier, Balingen (DE);
Hermann Goehl, Bisingen (DE);
Thomas Ertl, Bisingen (DE); Jacques Chevallet, Serezin du Rhône (FR);
Francesco Ribolzi, Varese (IT); Björn Frederik Seidler, Scheebel (DE);
Lennart Jönsson, Furulund (SE); Eddie Nilsson, Höör (SE)

(73) Assignee: Gambro Lundia AB, Lund (SE)

( * ) Notice: Subject to any disclaimer, the term of this patent is extended or adjusted under 35 U.S.C. 154(b) by 1084 days.

(21) Appl. No.: 10/595,546

(22) PCT Filed: Nov. 5, 2004

(86) PCT No.: PCT/EP2004/012528
§ 371 (c)(1),
(2), (4) Date: Sep. 8, 2008

(87) PCT Pub. No.: WO2005/044341
PCT Pub. Date: May 19, 2005

(65) Prior Publication Data
US 2009/0008310 A1  Jan. 8, 2009

(30) Foreign Application Priority Data

Nov. 7, 2003  (EP) ..................................... 03025640
Nov. 24, 2003  (EP) ..................................... 03026854
Nov. 24, 2003  (EP) ..................................... 03026855

(51) Int. Cl.
*B01D 19/00* (2006.01)
*B01D 63/00* (2006.01)
*A61M 1/36* (2006.01)
*C02F 1/20* (2006.01)
*C02F 1/44* (2006.01)

(52) U.S. Cl. ... 210/188; 210/239; 210/240; 210/321.71; 210/645; 422/45

(58) Field of Classification Search ........................ None
See application file for complete search history.

(56) References Cited

U.S. PATENT DOCUMENTS
4,227,420 A   10/1980  Lamadrid
(Continued)

FOREIGN PATENT DOCUMENTS
DE   4027531 C1   7/1991
(Continued)

OTHER PUBLICATIONS

WIPO, International Search Report, for PCT No. PCT/EP2004/012277, Published May 19, 2005, 3pgs.
(Continued)

*Primary Examiner* — Krishnan S Menon
*Assistant Examiner* — Dirk Bass
(74) *Attorney, Agent, or Firm* — Nixon & Vanderhye P.C.

(57) ABSTRACT

An integrated blood treatment module comprises a blood treatment device (1) having a housing (2) and a first end-cap (4) and a second end-cap (5) closing both ends of the housing (2). A pump hose (17) for a peristaltic pump has a first end (18) that is secured to the housing (2) and a second end (16) that is connected to a blood inlet port (15) of the first end-cap (4) so as to form a loop. A degassing device (30) is connected to the second end-cap (5). The degassing device (30), which, in use, is full of liquid, comprises a hydrophobic membrane through which bubbles and micro-bubbles escape the degassing device.

49 Claims, 11 Drawing Sheets

U.S. PATENT DOCUMENTS

| | | |
|---|---|---|
| 4,231,871 A | 11/1980 | Lipps et al. |
| 4,263,808 A | 4/1981 | Bellotti et al. |
| 4,287,059 A | 9/1981 | Kume et al. |
| 4,293,413 A | 10/1981 | Schnell |
| 4,344,777 A | 8/1982 | Siposs |
| 4,345,999 A | 8/1982 | Sigdell et al. |
| 4,368,118 A | 1/1983 | Siposs |
| 4,379,452 A | 4/1983 | DeVries |
| 4,412,916 A | 11/1983 | Kell |
| 4,433,971 A | 2/1984 | Lindsay et al. |
| 4,436,620 A | 3/1984 | Bellotti et al. |
| 4,479,760 A | 10/1984 | Bilstad et al. |
| 4,479,761 A | 10/1984 | Bilstad et al. |
| 4,479,762 A | 10/1984 | Bilstad et al. |
| 4,493,693 A | 1/1985 | Bilstad et al. |
| 4,582,598 A | 4/1986 | Bilstad et al. |
| 4,605,503 A | 8/1986 | Bilstad et al. |
| 4,617,115 A | 10/1986 | Vantard |
| 4,623,450 A | 11/1986 | Vantard et al. |
| 4,666,598 A | 5/1987 | Heath et al. |
| 4,676,467 A | 6/1987 | Palsulich |
| 4,765,888 A | 8/1988 | Barthe et al. |
| 4,770,787 A | 9/1988 | Heath et al. |
| 4,798,090 A | 1/1989 | Heath et al. |
| 4,806,135 A | 2/1989 | Siposs |
| 4,824,339 A | 4/1989 | Bainbridge et al. |
| 5,200,090 A | 4/1993 | Ford et al. |
| 5,441,636 A * | 8/1995 | Chevallet et al. ............ 210/232 |
| 5,468,388 A | 11/1995 | Goddard et al. |
| 5,707,431 A | 1/1998 | Verkaart et al. |
| 5,744,047 A | 4/1998 | Gsell et al. |
| 5,849,065 A | 12/1998 | Wojke |
| 6,176,903 B1 | 1/2001 | Wamsiedler |
| 6,206,954 B1 | 3/2001 | Schnell et al. |
| 6,361,518 B1 | 3/2002 | Brierton et al. |
| 6,582,386 B2 | 6/2003 | Min et al. |
| D479,320 S | 9/2003 | O'Mahony et al. |
| 2003/0138349 A1 | 7/2003 | Robinson et al. |

FOREIGN PATENT DOCUMENTS

| | | |
|---|---|---|
| EP | 0245782 A2 | 11/1987 |
| EP | 0292445 A1 | 11/1988 |
| EP | 0591896 A2 | 4/1994 |
| FR | 2513884 | 4/1983 |
| WO | WO-00/25843 A1 | 5/2000 |

OTHER PUBLICATIONS

WIPO, International Search Report, for PCT No. PCT/EP2004/012528 Published May 19, 2005, 4pgs.

WIPO, International Search Report, for PCT No. PCT/EP2004/011707 Published May 19, 2005, 2pgs.

WIPO, International Search Report, for PCT No. PCT/EP2004/012372 Published Jun. 16, 2005, 3pgs.

EPO, European Search Report, Application No. 1529545, Published Jun. 1, 2005, 3pgs.

EPO, European Search Report, Application No. 1530995, Published May 18, 2005, 2pgs.

EPO, European Search Report, Application No. 1532994, Published May 25, 2005, 3pgs.

* cited by examiner

INTEGRATED BLOOD TREATMENT MODULE

The present invention relates to an integrated extracorporeal blood treatment circuit, in particular for extracorporeal blood treatments using a filter.

Filters are used in various extracorporeal treatments of blood, such as hemodialysis, hemofiltration, hemodiafiltration, plasmapheresis. The same type of filter, usually referred to as hemodialyzer or hemofilter, is used for hemodialysis, hemofiltration, hemodiafiltration. The main difference between a hemodialyzer and a plasmafilter (i.e. a filter used in plasmapheresis) is the pore size of their respective membrane, a membrane for plasmapheresis allowing the proteins contained in blood to migrate therethrough, whereas a membrane for hemodialysis does not.

A conventional filter for extracorporeal treatment of blood comprises a first and a second compartments separated by a membrane, the first compartment having an inlet and an outlet for the circulation of blood therethrough and the second compartment having an outlet for draining a liquid (e.g. plasma water, plasma, used dialysis liquid) and an inlet when the treatment (e.g. hemodialysis) requires the circulation of a treatment liquid (e.g. a dialysis liquid) in the second compartment. The membrane is enclosed in an elongated tubular housing closed at both ends by an end-cap having a nozzle used as an inlet/outlet port for the first compartment.

In the above treatments, blood is withdrawn from the patient, flown through the first compartment of the filter, and returned to the patient. In hemodialysis, a dialysis liquid is simultaneously flown though the second compartment of the filter and the metabolic wastes (urea, creatinine) contained in blood migrate by diffusion through the membrane into the second compartment. In hemofiltration, a pressure difference is created across the membrane so that plasma water flows through the membrane into the second compartment of the filter. Here, metabolic wastes migrate by convection into the second compartment. In order to compensate for the loss of bodily fluid, the patient is simultaneously infused a sterile substitution solution. Hemodiafiltration is a combination of hemodialysis and hemofiltration, and, in this treatment, a dialysis liquid is flown through the second compartment and a substitution liquid is infused into the patient. In plasmapheresis, a pressure difference is created across the membrane so that plasma (i.e. plasma water and proteins) flows through the membrane into the second compartment of the filter. Once treated, the plasma is returned to the patient.

A machine for performing any of the above treatments comprises a peristaltic pump for withdrawing blood from a patient through a so-called "arterial" line connected at one end to the vascular circuit of the patient and at the other end to the inlet of the first compartment of a filter, for pumping blood into the filter, and for returning blood to the patient through a so-called "venous" line connected at one end to the outlet of the first compartment of the filter and at the other end to the vascular circuit of the patient. The treatment machine also usually comprises a first blood pressure sensor for measuring the pressure of blood in the arterial line upstream of the pump, a second blood pressure sensor for measuring the pressure of blood in the arterial line downstream of the pump, a third pressure sensor for measuring the pressure of blood in the venous line, a bubble detector for detecting air bubbles in the venous line and a clamp for closing the venous line, for example when air bubbles are detected by the bubble detector.

An arterial line typically comprises the following components connected together by segments of flexible tubes: a first Luer connector for connection to an arterial cannula, an arterial bubble trap, a pump hose for cooperating with the rotor of the peristaltic pump of the treatment machine, and a second Luer connector for connection to the inlet of the first compartment of the filter.

A venous line typically comprises the following components connected together by segments of flexible tubes: a first Luer connector for connection to the outlet of the first compartment of the filter, a venous bubble trap, and a second Luer connector for connection to a venous cannula. Usually, the first and third pressure sensors of the machine are connected to the arterial and venous bubble traps respectively, when the treatment machine, the arterial line, the venous line and the filter are assembled in view of a treatment.

A conventional bubble trap is basically an elongated container that, in use, is held vertically. The container has an inlet and an outlet for blood that are arranged so as not to be adjacent. It comprises also, in an upper location, a pressure measuring port for connection to a pressure sensor, an infusion port for infusing a liquid (e.g. a drug or a sterile saline solution) and an injection port for adding or removing air into or from the bubble trap so as to adjust the level of blood therein. In use, the bubble trap contains a volume of blood in a lower part that transiently stagnates therein so as to let gas bubbles and micro bubbles escape by gravity and join an upper part of the container full of air. In a conventional bubble trap, there is therefore always an interface blood-air. In order to properly operate, conventional bubble traps must contain a certain volume of blood (which conflicts with the long lasting effort of minimizing the extracorporeal volume of blood in blood treatments). Also their use is limited to relatively short treatment sessions because of the blood clotting resulting from the permanent blood-air interface. In this respect, they are adapted to chronic treatment (a treatment session for a chronic patient usually lasts about four hours), but they cannot be used for intensive care treatment (the treatment of an acute patient can last several days).

The assemblage of an extracorporeal blood circuit as described above (i.e. the connection of the arterial and venous lines to, the filter), the mounting thereof on a blood treatment machine, and the setting of the liquid level in the bubble traps is relatively time consuming.

An object of the invention is to design an integrated blood treatment module that can be mounted on a treatment machine faster than a conventional extracorporeal blood circuit and can be used for long lasting treatments.

According to the invention, an integrated blood treatment module comprises:
  a blood treatment device having:
  a housing having a longitudinal axis;
  a first end-cap closing a first end of the housing, the first end-cap having a blood inlet port;
  a second end-cap closing a second end of the housing;
  a pump hose for a peristaltic pump, wherein the pump hose has a first end that is secured to the housing and a second end that is connected to the blood inlet port so that the pump hose extends in a position that is complementary to the position of a race of the peristaltic pump; and
  a degassing device connected to the second end-cap having:
  a first chamber having an inlet for receiving a liquid flowing into the second end-cap, and
  a second chamber having an opening closed by a hydrophobic membrane and an outlet for discharging the liquid,
wherein the first chamber has a downstream portion that partially extends within the second chamber and communicates therewith by a passageway, and the second chamber has a downstream portion that extends below the passageway and asymmetrically surrounds the downstream portion of the first chamber.

Additional features are as follows:

The integrated blood treatment module comprises a first pressure measurement chamber that is secured to the blood treatment device and is connected to the first end of the pump hose, the first pressure measurement chamber having a pressure measurement port for connection to a pressure sensor, the pressure measurement port having a central axis that is parallel to a central axis of at least one access port of the housing.

The integrated blood treatment module comprises a second pressure measurement chamber that is secured to the blood treatment device and is connected to the outlet port of the blood degassing device, the second pressure measurement chamber having a pressure measurement port for connection to a pressure sensor, the pressure measurement port having a central axis that is parallel to a central axis of at least one access port of the housing.

The integrated blood treatment module comprises a third pressure measurement chamber that is secured to the blood treatment device and is connected to the second end of the pump hose, the third pressure measurement chamber having a pressure measurement port for connection to a pressure sensor, the pressure measurement port having a central axis that is parallel to a central axis of at least one access port of the housing.

The integrated blood treatment module according to the invention presents several advantages. First, it is compact and allows for a significant reduction of the extracorporeal blood volume that is needed in extracorporeal blood treatments. Second, it does not require any specific activity for its mounting on a treatment machine nor for its setting in use (in particular, no adjustment of the level of the air-blood interface is needed in the degassing device). Third, since the degassing device operates without air-blood interface, the integrated blood circuit is particularly adapted to long lasting treatments (e.g. continuous renal replacement therapies).

Other additional or alternative features of the invention are as follows:

The integrated blood treatment module comprises a support structure having a plurality of conduits defined therein, the blood treatment device being secured to the support structure.

The support structure comprises a first conduit having a first end connected to a first access port of the housing, and a second end comprised of an outlet nozzle for a waste liquid.

The support structure comprises a second conduit having a first end connected to a second access port of the housing, and a second end comprised of an inlet nozzle for a dialysis liquid.

The support structure comprises:
a third conduit having an inlet for connection to a blood withdrawal tube, and an outlet connected to the first end of the pump hose; and
a fourth conduit having an inlet connected to the second end of the pump hose, and an outlet connected to the blood inlet port of the first end-cap.

The support structure comprises a sixth conduit having a first end connected to the fourth conduit and a second end for connection to a pre-dilution infusion tube.

The integrated blood treatment module comprises a first pressure measurement chamber defined within the support structure and connected to the third conduit for measuring a pressure upstream of the pump hose.

The outlet of the third conduit and the inlet of the fourth conduit are arranged with respect to each other so that the pump hose forms a loop that extends in a plane substantially parallel to the longitudinal axis of the housing.

The outlet of the third conduit is located between the two end-caps and the loop formed by the pump hose extends laterally with respect to the housing of the blood treatment device.

The outlet of the third conduit is located along the longitudinal axis of the housing beyond the first end-cap, and the loop formed by the pump hose is offset along the longitudinal axis of the housing with respect to the housing of the blood treatment device.

The outlet of the third conduit and the inlet of the fourth conduit are arranged with respect to each other so that the pump hose forms a loop that extends in a plane inclined with respect to a plane substantially perpendicular to the longitudinal axis of the housing.

The support structure comprises a fifth conduit having an inlet connected to the outlet port of the blood degassing device, and an outlet for connection to a blood return tube.

The support structure comprises a seventh conduit having a first end connected to the fifth conduit and a second end for connection to a post-dilution infusion tube.

The integrated blood treatment module comprises a second pressure measurement chamber defined within the support structure and connected to the fifth conduit for measuring a pressure downstream of the blood degassing device.

The first pressure measurement chamber has a port for connection to a pressure sensor, the second pressure measurement chamber has a port for connection to a pressure sensor, and wherein the inlet nozzle, the outlet nozzle, the port of the first pressure measuring chamber and the port of the second measuring chamber have respective central axes that are substantially parallel.

The respective central axes of the inlet nozzle, of the outlet nozzle, of the port of the first pressure measuring chamber and of the port of the second measuring chamber are substantially perpendicular to the longitudinal axis of the housing.

The downstream portion of the second chamber has a lateral wall that surrounds a longitudinal axis of the degassing device and a bottom wall that is inclined with respect to a longitudinal axis of the degassing device.

The downstream portion of the first chamber has a lateral wall that is concentric to the lateral wall of the second chamber.

The lateral wall of the downstream portion of the first chamber and the lateral wall of the downstream portion of the second chamber are substantially cylindrical.

The downstream portion of the first chamber has a cross-section that is substantially the same as the cross-section of the passageway between the first and the second chamber.

The first chamber comprises an upstream portion having a decreasing cross section.

The second chamber comprises an upstream portion extending above the passageway that has a decreasing cross-section, with a larger cross-section that is substantially level with the passageway and a smaller cross-section that is substantially level with the hydrophobic membrane.

The upstream portion of the second chamber is substantially frusto-conical.

The outlet port opens in the downstream portion of the second chamber at a location furthest to the passageway.

The first chamber of the degassing device has a downstream portion having a cross-section selected with respect to a maximal flow rate of a liquid in the module so that the velocity of the liquid in the downstream portion of the first chamber is less than a predetermined velocity.

The cross-section of the downstream portion of the first chamber is selected with respect to a maximal flow rate of a liquid of about 500 ml/min in the module so that the velocity of the liquid in the downstream portion of the first chamber is less than about 3 m/min.

The cross-section of the second chamber of the degassing device at the level of the passageway is selected so that the ratio of the velocity of a liquid within a downstream portion of the first chamber to the velocity of the liquid within the second chamber at the level of the passageway is more than a determined value.

The cross-section of the second chamber of the degassing device at the level of the passageway is selected so that the ratio of the velocity of the liquid within the downstream portion of the first chamber to the velocity of the liquid within the second chamber at the level of the passageway is at least about 2.

The downstream portion of the second chamber forms an overflow for a fluid flowing from the first chamber into the second chamber.

The first chamber, the second chamber and the passageway therebetween are arranged with respect to each other so that a flow pattern of a liquid flowing from the first chamber, through the second chamber and to the outlet port comprises a component that is tangential to the membrane.

The flow pattern of a liquid flowing from the first chamber, through the second chamber and to the outlet port comprises an umbrella like component.

The first chamber, the second chamber and the passageway therebetween are arranged with respect to each other so that a flow of liquid flowing from the first chamber, through the second chamber and to the outlet port keeps gas bubbles in motion along an inner surface of the hydrophobic membrane.

The integrated blood treatment module comprises a protective member for protecting the hydrophobic membrane against external blows and for limiting the deformation of the hydrophobic membrane when the pressure of the liquid within the degassing device exceeds a limit.

The hydrophobic membrane is arranged in a plane substantially perpendicular to a longitudinal axis of the degassing device.

The blood degassing device that is part of the integrated blood treatment module according to the invention is very efficient and remains efficient over time. Also its allows for a compact design, i.e. a small internal volume. For example, It is possible to design such degassing device with a total internal volume that is about half of the blood volume in conventional bubble traps.

Other features and advantages of the invention will appear on reading the detailed description that follows. Reference will be made to the appended drawings in which.

Figure 1:
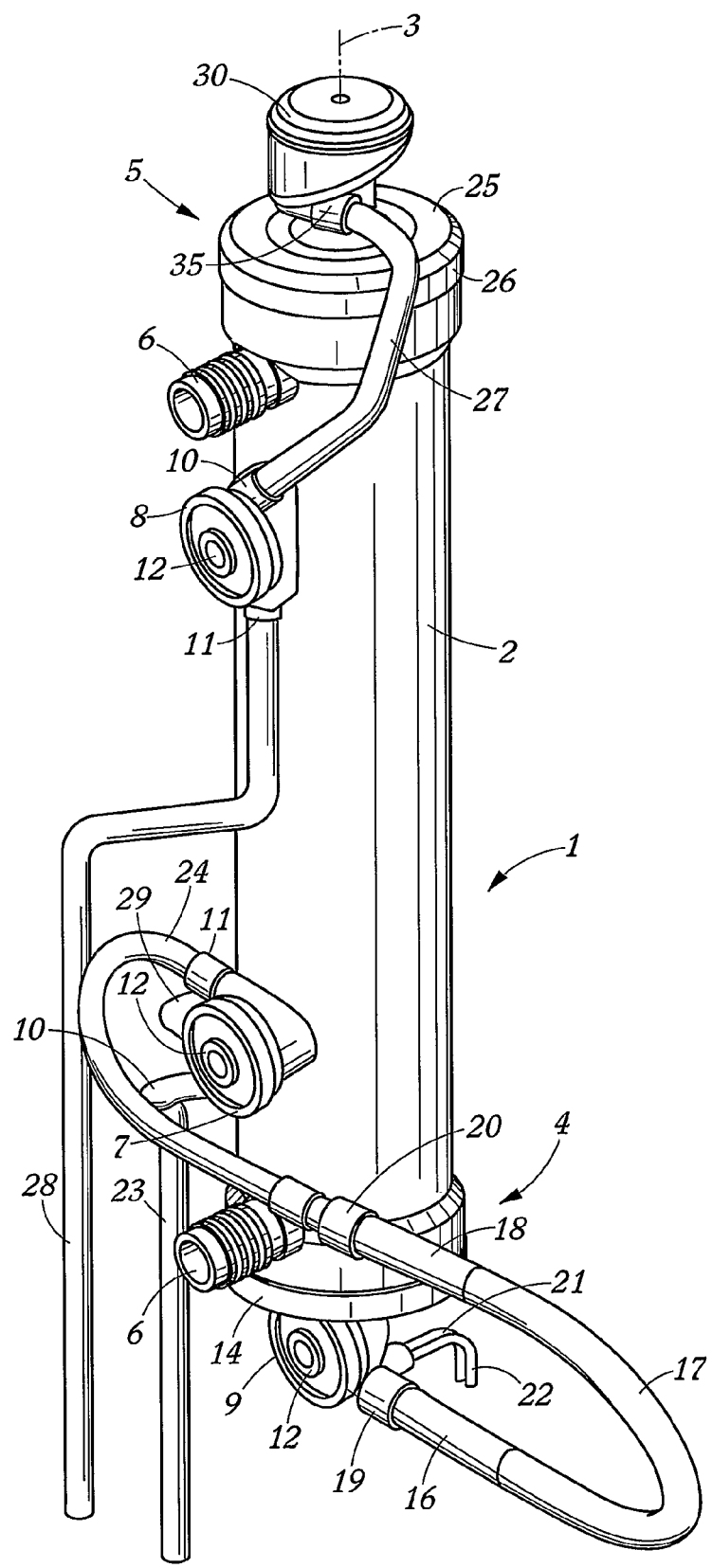
FIG. 1 is a perspective view of a first embodiment of the integrated blood treatment module according to the invention.
Figure 2:
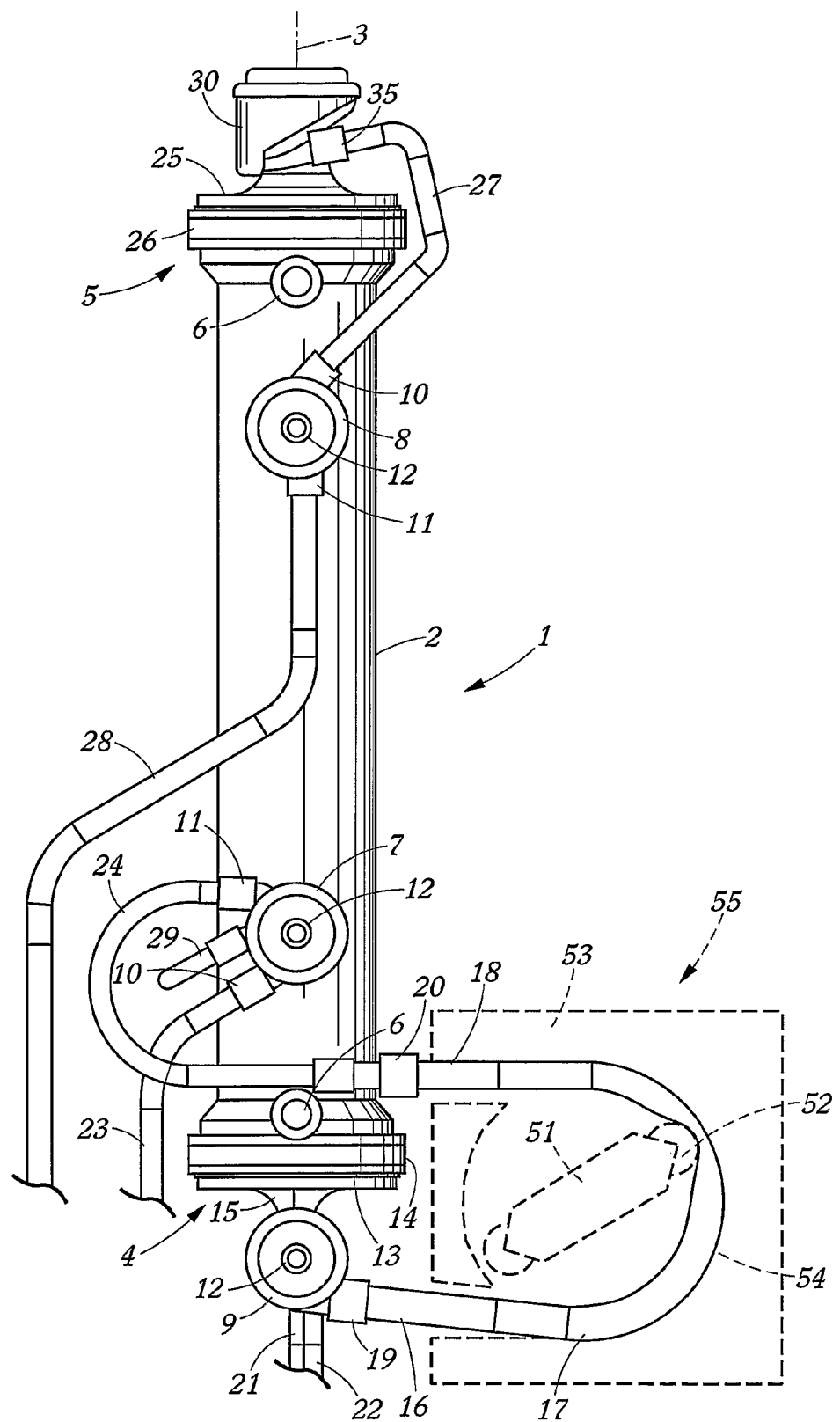
FIG. 2 is a front view of the integrated blood treatment module of FIG. 1.

FIGS. 1 and 2 show an integrated blood treatment module comprising a blood treatment device in the form of a hollow fiber filter 1 having a tubular housing 2 closed at one end by a lower end-cap assembly 4 and at the other end by an upper end-cap assembly 5 (in use, the integrated blood treatment module is held in a substantially vertical position, and the end-cap assemblies are referred to here by the respective position they occupy along a vertical line when the integrated blood treatment module is in use). The tubular housing 2, which has a longitudinal axis 3, contains a semi-permeable membrane composed of a bundle of hollow fibers extending within the housing 2 and secured thereto at both ends by a potting compound in which they are embedded. The potting compound forms a disk that extends perpendicularly to the longitudinal axis 3 of the housing 2. The ends of the fibers open on an outer surface of the disks of potting material.

By construction, the hollow fiber filter 1 comprises a first and a second compartments separated from each other by the semi-permeable membrane. The first compartment includes the interior of the hollow fibers and the space delimited at each end of the filter between the outer surface of the disk of potting compound and the inner surface of the end-cap assemblies 4, 5, and the second compartment includes the space outside of the hollow fibers that is delimited by the inner surface of the housing and the inner surface of the disks of potting material. The housing 2 is fitted at both ends with nozzles 6 that give access to the second compartment. The central axis of the nozzles 6 are perpendicular to the longitudinal axis 3 of the housing 2.

A first and a second disk-shaped blood pressure measuring chambers 7, 8 are secured to the housing 2 at the vicinity of the two nozzles 6 respectively. Each blood pressure measuring chamber 7, 8 comprises a blood compartment and an air compartment separated by a circular flexible membrane. The blood compartment comprises an inlet port 10 and an outlet port 11. An infusion port 29 for a medical or pharmaceutical liquid is connected to the blood compartment of the first blood pressure measuring chambers 7. The air compartment comprises a measurement port 12 for connection to a pressure sensor. The blood pressure measuring chambers 7, 8 are secured to the housing 2 so that the measurement ports 12 and the nozzles 6 open in the same direction. The central axis of the nozzles 6 and the central axis of the measurement ports 12 are substantially parallel and they are substantially perpendicular to the longitudinal axis 3 of the housing 2.

The lower end-cap assembly 4 comprises a circular end-wall 13 connected to a tubular peripheral wall 14 by which the end-cap 4 is secured to the housing 2. The end-wall 13 is substantially perpendicular to the longitudinal axis 3 of the filter 1 and the tubular peripheral wall 14 is concentric to the housing 2. The end wall 13 is fitted with an inlet nozzle 15 connected to the end-wall 13 so that the central axis of the nozzle 15 coincides with the longitudinal axis 3 of the housing 2. The lower end-cap assembly 4 further comprises a third blood pressure measuring chamber 9 similar to the first and second blood pressure measuring chambers 7, 8. The outlet of the blood compartment of the third pressure measuring chamber 9 is physically and fluidly connected to the inlet nozzle 15, and the inlet thereof is physically and fluidly connected to a tubular connector 19 dimensioned for receiving a downstream end 16 of a pump hose 17. The measurement port 12 of the air compartment of the pressure measurement chamber 9 is oriented like the nozzles 6 and the measurement ports 12 of the first and second pressure measuring chamber 7, 8, i.e. its axis is perpendicular to the longitudinal axis 3 of the housing 2.

A first tube 21 for infusion of an anticoagulant liquid (e.g. heparin) and a second tube 22 for infusion of a medical or pharmaceutical liquid are connected to the pump hose connector 19.

The upstream end 18 of the pump hose 17 is connected to a tubular connector 20 secured to the housing 2 just above the lower nozzle 6. The two pump hose connectors 19 and 20 are so oriented that a pump hose 17 connected thereto forms a U-shaped loop that extends in a plane perpendicular to a plane containing the axes of the nozzles 6 and inclined with respect to the longitudinal axis 3 of the filter 1.

As diagrammatically shown in FIG. 2, the looped pump hose 17 is adapted to readily cooperate with a peristaltic pump of the rotary type included in a treatment machine (e.g. a dialysis machine). It is recalled that a conventional rotary peristaltic pump 55 comprises a rotor 51 generally bearing two rollers 52 at its periphery. The rotor 51 is mounted in a support 53 having a semi-circular wall 54 that partially surrounds the rotor and defines a race against which a pump hose 17 can be received. When the rotor rotates, the rollers 52 alternately engage the pump hose 17 and squeeze it against the semi-circular race 54 while moving along a circular path, thereby pushing the liquid contained in the pump hose 17 towards the downstream end 16 thereof.

A blood withdrawal tube (or arterial line) comprises a first segment 23 connected to the inlet 10 of the first pressure measuring chamber 7 and a second segment 24 connecting the outlet 11 of the first pressure measuring chamber 7 to the tubular connector 20, that is to the pump hose 17. The first pressure measuring chamber 7 is therefore used to measure the blood pressure upstream of the pump hose (so-called "arterial" pressure).

The upper end-cap assembly 5 comprises an annular end-wall 25 connected to a tubular peripheral wall 26 by which the end-cap 5 is secured to the housing 2. The end-wall 25 is substantially perpendicular to the longitudinal axis 3 of the filter 1 and the tubular peripheral wall 26 is concentric to the housing 2. The upper end-cap assembly 5 also comprises a blood degassing device 30 that is connected to the annular end-wall 25. The blood degassing device 30, which is shown in details in FIGS. 3 and 4, comprises an outlet port 35 that is connected by a first segment 27 of a blood return tube (or venous line) to the inlet 10 of the second pressure measurement chamber 8. The blood return tube comprises a second segment 28 that is connected to the outlet 11 of the second pressure measurement chamber 8. The first pressure measuring chamber 7 is therefore used to measure the blood pressure downstream of the filter (so-called "venous" pressure).

Figure 3:
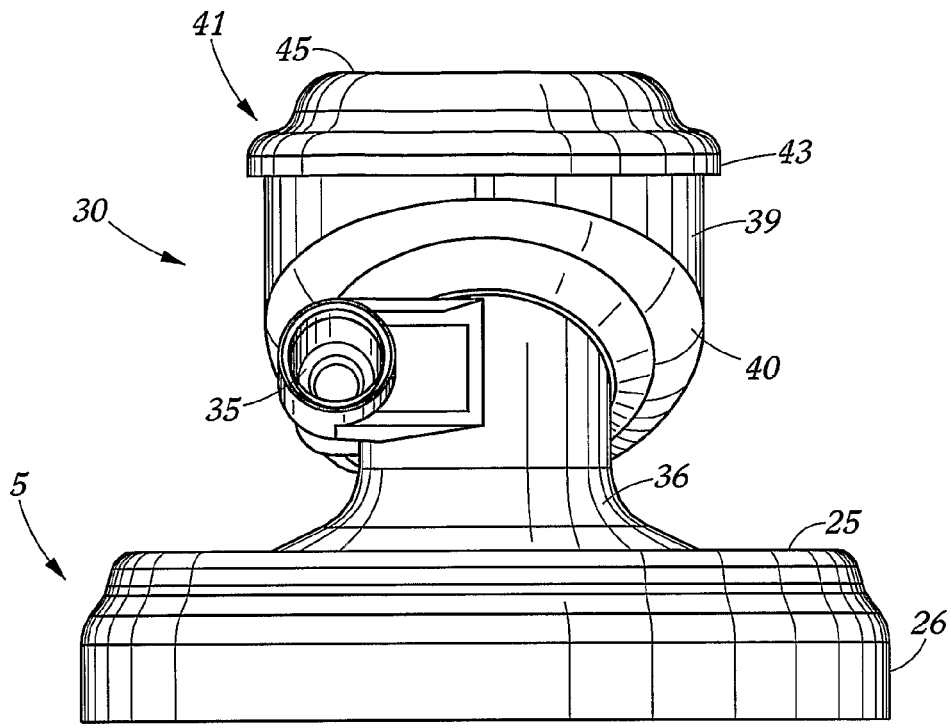
FIG. 3 is a front view of the upper end-cap assembly of the integrated blood treatment module of FIG. 1.
Figure 4:
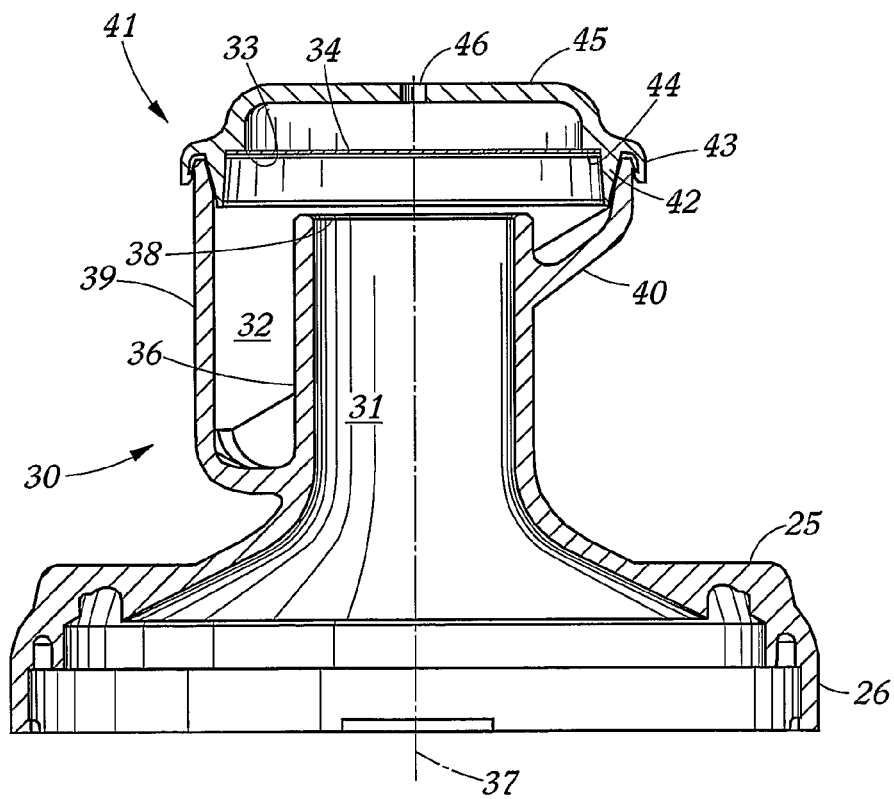
FIG. 4 is a cross-section view of the upper end-cap assembly of FIG. 3, along a plane that contains the central axis of the end-cap.

As shown in FIGS. 3 and 4, the degassing device 30 comprises a first chamber 31 for receiving a liquid flowing out of the first compartment of the filter 1 into the end-cap assembly 5; a second chamber 32 in communication with the first chamber 31 and having an opening 33 closed by a hydrophobic membrane 34; and the outlet port 35, which is connected to the second chamber 32, for discharging the liquid.

The first chamber 31 is delimited by a funnel like wall 36 having a first end of larger cross section, by which it is connected to the end-wall 25 of the end-cap 5, and a second end of smaller cross section, which defines a passageway 38 between the first chamber 31 and the second chamber 32. The funnel like wall 36 is centered on a longitudinal axis 37 of degassing device 30. In the direction of the flow, the first chamber 31 has therefore an upstream portion having a decreasing cross-section and a downstream portion having a constant cross-section (unless otherwise specified, "cross-section" means here and hereunder the transversal cross-section with respect to the longitudinal axis 37; also, the "direction of flow" means the direction of flow from the first compartment of the filter 1 to the outlet port 35 through the first and the second chambers 31, 32 of the degassing device 30).

In the direction of flow, the second chamber 32 of the degassing device 30 comprises a disk-shaped upstream portion extending above the passageway 38 and a downstream portion extending below the passageway 38 and partially and asymmetrically surrounding the downstream portion of the first chamber 31. The downstream portion of the second chamber 32 is delimited by a cylindrical wall 39 that is concentric to the cylindrical portion of the wall 36 of the first chamber 31, and by a substantially flat bottom wall 40 that is beveled of about 45 degrees with respect to the axis 37. The highest point of the oblique bottom wall 40 is adjacent to the rim of the cylindrical wall 39. It results from the respective arrangement of the first chamber 31 and of the downstream portion of the second chamber 32 that the second chamber 32 forms an overflow for a liquid flowing from the first chamber 31 into the second chamber 32.

The outlet port 35 of the degassing device 30 is comprised of a tubular wall that is connected to the inclined wall 40 of the second chamber 32, at a lower point thereof. The central axis of the outlet port 35 is substantially perpendicular to the longitudinal axis 37 of the degassing device 30. The outlet port 35 extends inwardly, that is below the inclined wall 40 of the second chamber 22, tangentially to the upper cylindrical portion of the wall 36 of the first chamber 31.

It results from the shape of the second chamber 32 (cylindrical wall 39 connected to a slanting bottom wall 40), and from the connection of the outlet port 35 at the lowest point thereof, two characteristics that are of particular interest for a degassing device intended for blood: in comparison to a second chamber that would completely and symmetrically surround the first chamber or even only the upstream cylindrical portion of the first chamber, with a bottom wall substantially perpendicular to the longitudinal axis of the degassing device, the design represented in the figures allows for a degassing device having a minimal internal volume, and in which there is no area of relative stagnation for a liquid circulated through the degassing device. It was observed during the research work that led to the present invention, that with a second chamber completely surrounding the first chamber, with a bottom wall substantially perpendicular to the longitudinal axis of the degassing device, an area of relative stagnation appears in the second chamber opposite to the outlet port.

The disk-shaped upstream portion of the second chamber 32 is defined within a capsule like lid 41 fitting on the upper rim of the cylindrical wall 39 of the second chamber 39. More specifically, the disk-shaped upstream portion of the second chamber 32 is delimited by an inner peripheral wall 42 of the lid 41, which has a frusto-conical inner surface, and by a circular hydrophobic membrane 34 closing an opening of the second chamber 32 within the lid 41 defined by an inner annular shoulder 33. The hydrophobic membrane 34 is secured (e.g. by gluing) at its periphery to the shoulder 33 and is perpendicular to the axis 37 of the degassing device 30. In more details, the capsule like lid 41 comprises a circular flat top wall 45 connected to the inner peripheral wall 42 and to an outer peripheral wall 43. The inner peripheral wall 42 and the outer peripheral wall 43 define therebetween a groove corresponding to the upper rim of the cylindrical wall 39 of the second chamber 32, so that the lid 41 can be engaged into the rim of the cylindrical wall 39 and secured thereto, e.g. by gluing. The lid 41 also comprises a vent 46 in the middle of the circular flat top wall 45 through which the air removed from the liquid in the degassing device 30 can escape. The annular shoulder 33 is spaced apart from the top wall 45 of the lid 41 so that the hydrophobic membrane 34 can deform under positive pressure. The top wall 45 of the lid 41 essentially protects the hydrophobic membrane 34 against outside blows.

It results from the respective arrangement of the first chamber 31 and of the of the second chamber 32 that a liquid circulated through the degassing device 30 has an umbrella pattern with a longitudinal component within the first chamber 31 and a radial component within the upstream portion of the second chamber 32. The radial component of the flow tangentially sweeps the hydrophobic membrane 34 and helps prevent the formation of blood foam along its internal surface while keeping bubbles and micro bubbles in constant motion along the membrane until they escape therethrough.

Its is possible to optimize the efficiency of the degassing device of the invention by selecting the diameter of the downstream cylindrical part of the first chamber 31 (wall 36) with respect to the maximal flow rate of blood within the integrated blood treatment module, as well as the size of the second chamber 32 (diameter of the cylindrical wall 39) with respect to the size of the first chamber 31 (diameter of the cylindrical wall 36) so that:
  the maximal velocity of the liquid in the first chamber 31 (corresponding the maximal flow rate in the blood treatment module) is never high enough to prevent the bubbles and micro-bubbles from migrating towards the hydrophobic membrane 34 and to expel them to the outlet port 35; and
  the velocity of the liquid entering the second chamber decreases to such an extent that bubbles and micro-bubbles can migrate by gravity towards the hydrophobic membrane 34.

For example, for a maximal blood flow rate of about 500 ml/min within the blood treatment module, it was determined during the researches that led to the invention that an optimal velocity of blood within the downstream portion of the first chamber 31 (cylindrical wall 36) should be less than about 3 ml/min and that the optimal ratio of the velocity of blood within the downstream portion of the first chamber 31 to the velocity of blood within the second chamber 32 at the level of the passageway 38 should be at least about 2.

Figure 5:
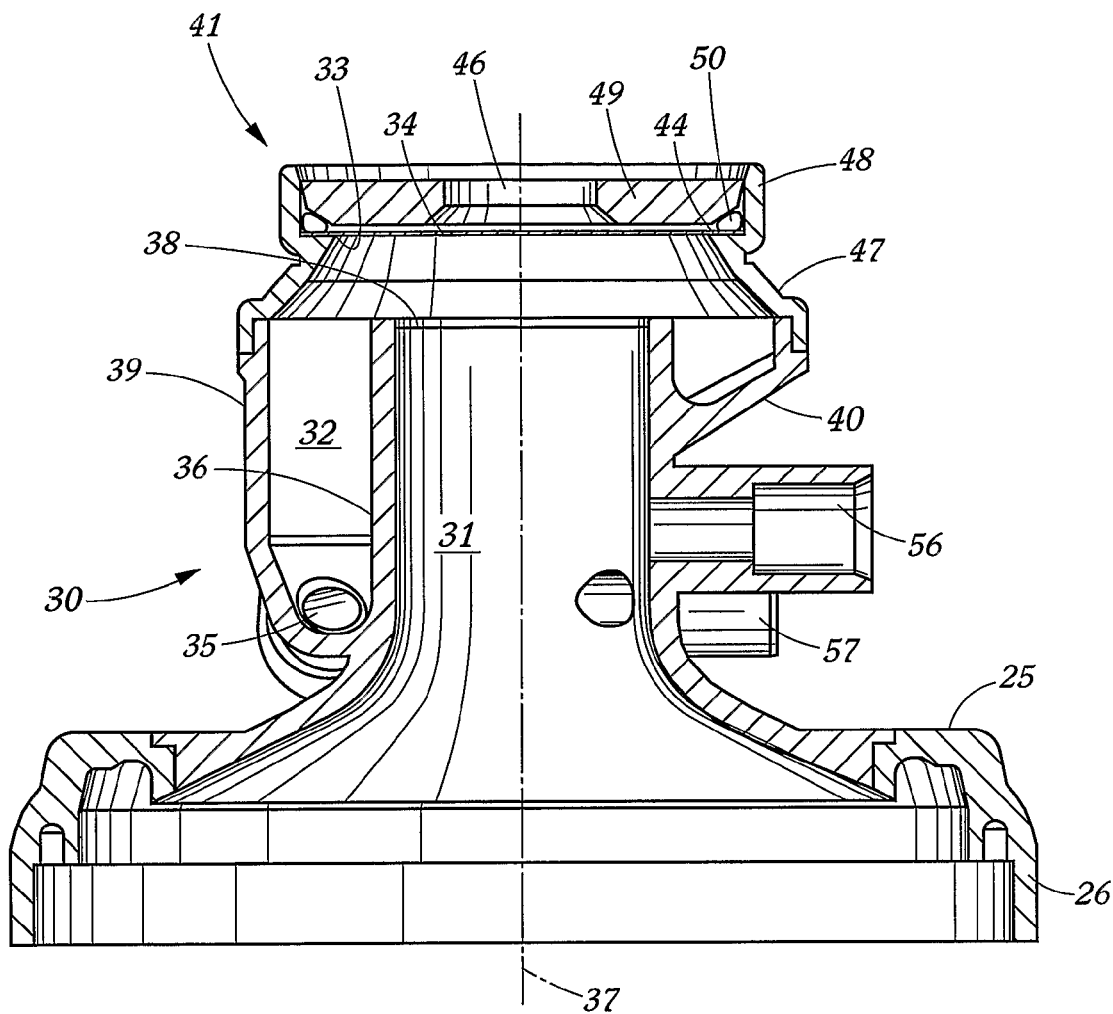
FIG. 5 is a cross-section view a second embodiment of an upper end-cap assembly, along a plane that contains the central axis of the end-cap.

FIG. 5 shows a second embodiment of an upper end-cap assembly 5, which is a variant of the end cap assembly shown in FIGS. 3 and 4.

In this second embodiment, the upstream portion of the second chamber 32 is delimited by a lid 41 having a lower rim that is so dimensioned as to snugly engage an outer annular rabbet of the upper rim of the cylindrical wall 39. The lid 41 comprises a first, frusto-conical, wall 47 connected to a second, cylindrical, wall 48, the first wall 47 being connected to the second wall 48 by its smaller section. Note that the first wall 47 comprises in fact two frusto-conical portions, the lower portion having an angle that is slightly larger than the angle of the upper portion. The upstream portion of the second chamber 32 has therefore a decreasing cross-section. The lid 41 further comprises an inner annular shoulder 44 that extends at the junction between the frusto-conical wall 47 and the cylindrical wall 48. The aperture defined by the inner annular shoulder 44 forms an opening 33 of the second chamber 32 that is closed by the hydrophobic membrane 34. The membrane 34 is secured to the annular shoulder 44 by an O-ring 50 resting at the periphery of the membrane 34 and against which a disk-shaped stopper 49 is tightly engaged. The stopper 49, which snugly fits within the cylindrical wall 48 of the lid 41, comprises a vent 46 in its center through which the air removed from the liquid in the degassing device 30 can escape. Note that the membrane 34 is close but does not abut on the inner surface of the stopper 49. The membrane 34 can therefore deform to a certain extent. When the positive pressure in the filter exceeds however a determined value, the membrane 34 abuts on the stopper 49 and does not run the risk of rupturing.

Also, In the second embodiment of the upper end-cap assembly 5 shown in FIG. 5, two inlet ports 56, 57 are connected to the first chamber 31. The ports 56, 57 can be used for the infusion of various liquid (e.g. a substitution liquid or a drug, when the filter is a hemofilter) and for connection to a pressure sensor.

A prototype of the degassing device 30 shown in FIG. 5 was made of molded polycarbonate: the diameter of the downstream portion of the first chamber 31 (cylindrical part of wall 36) was 16 mm; the inner diameter of the second chamber 32 at the level of the passageway 38 was 19 mm; the outer diameter of the second chamber 32 at the level of the passageway 38 was 32 mm; the diameter of the hydrophobic membrane 34 (useful surface) was 27 mm; the distance between the passageway 38 and the hydrophobic membrane 34 was 5 mm. The membrane was made of polytetrafluoroethylene and had a thickness of 0,13 mm and a pore size of 0.2 µm.

Bovine blood was circulated at a flow rate of 500 ml/mn in a closed loop circuit including a hemofilter connected to the prototype of degassing device 41. The velocity of blood within the degassing device was:
  2,5 m/min in the downstream cylindrical portion of the first chamber 31;
  2 m/min between the passageway 38 and the hydrophobic membrane 34;
  1 m/min in the downstream portion of the second chamber 32, just below the level of the passageway 38; and
  2 m/min in the downstream portion of the second chamber 32, just upstream of the outlet port 35.

The pressure in the degassing device was 50 mmHg. After four hours, 5 ml of air was injected in the circuit upstream of the hemofilter. After 15 minutes, the air injected in the circuit had been totally removed by the degassing device 30.

The end-cap 25, 26, the walls 36, 39 and 40 that delimit the first chamber 31 and the downstream portion of the second chamber 32, and the ports 25 (56, 57), connected thereto, can be made by molding in one piece from a plastic material. A biologically inert material like polycarbonate is appropriate when the filter is for medical use. The lid 41 can also be made in one piece by molding, from the same material as the end-cap 25, 26 and the walls 36, 39 and 40. The hydrophobic membrane 34 can be made of polytetrafluoroethylene.

The operation of the integrated blood treatment module 1 is as follows.

Before a treatment session, the integrated blood treatment module 1 is secured to a treatment machine in a substantially vertical position, with the degassing chamber 30 being in the upper position. The two nozzles 6 of the second compartment of the filter are respectively connected to a dialysis liquid supply conduit and to a waste liquid conduit of the treatment machine. The pressure measurement ports 12 of the first, second and third blood pressure measurement chambers 7, 8, 9 are respectively connected two an arterial pressure sensor, a post-pump/pre-filter pressure sensor and a venous pressure sensor of the treatment machine. The pump hose 17 is engaged between the rotor 51 and the circular race 54 of a peristaltic pump 55 of the treatment machine. A bag of sterile saline solution is connected to the blood withdrawal tube 23 and an empty waste bag is connected to the blood return tube 28. The sterile saline solution is then pumped by the peristaltic pump 55 into the blood withdrawal tube 23, and through the first pressure measurement chamber 7, the pump hose 17, the third pressure measurement chamber 9, the first compartment of the filter 1, the degassing device 30, the second pressure measurement chamber 8 and the blood return tube 28, so as to rinse the extracorporeal blood circuit, to fill it with sterile saline solution and to remove air therefrom (preparatory steps called "priming" of the extracorporeal blood circuit). At the end of this process, there is no more air in the integrated blood treatment module 1, in particular in the degassing device 30. Then, the blood withdrawal tube 23 is connected to a blood vessel of a patient, blood is pumped into the extracorporeal circuit while the saline solution flowing out of the venous line 28 is collected in the waste bag. When blood reaches the end of the blood return tube 28, the blood return tube is in turn connected to the vessel of the patient and the treatment proper can start.

In the filter 1, the blood flows within the hollow fibers, enters the end-cap assembly 5, flows through the first chamber 31, pours into the second chamber 32 and leaves the degassing device 30 via the outlet port 35. Since the cross-section of the second chamber 32 at the level of the passageway 38 is substantially larger than the cross-section of the passageway 38 itself, the blood flow substantially decreases when blood enters the second chamber 32. This helps the bubbles and micro-bubbles that may be present in blood to move upwards by gravity towards the hydrophobic membrane 34. Also, because blood is directed by the funnel like wall 36 towards the hydrophobic membrane 34 and from then towards the frusto-conical wall 42 (47 in FIG. 5) of the lid 41, the overall flow pattern of blood is umbrella like with a component that is tangential to the hydrophobic membrane 34. The membrane is therefore permanently swept and the creation of a layer of static blood foam on the inner surface of the membrane 34 is prevented. Instead, the bubbles and micro-bubbles are kept in a permanent motion at the vicinity of the membrane 34, through which they pass shortly after entering the second chamber 32.

FIGS. 6 to 9 show a second embodiment of the integrated blood treatment module according to the invention. This integrated blood treatment module comprises a support structure 60 having a plurality of conduits defined therein, a filter 100 and a blood degassing device 30 that are secured to the structure 60.

The filter 100 has the same overall construction as the filter 1 described above, save for the identical end-caps 101 that are closing its housing 2 at both ends. Each end-cap 101 comprises a circular end-wall 102 connected to a tubular peripheral wall 103 by which the end-cap 101 is secured to the housing 2. The end-wall 102 is substantially perpendicular to the longitudinal axis 3 of the filter 100 and the tubular peripheral wall 103 is concentric to the housing 2. The end-cap assembly 101 also comprises an inlet nozzle 104 (or outlet nozzle 105) that is connected to the end-wall 102 so as to extends radially with respect to the longitudinal axis 3 of the housing 2. The end-caps 101 are mounted on the housing 2 so that the inlet and outlet nozzles 6, 104, 105 of the first and second compartments of the filter 100 extend parallel to each other on the same side of the filter 1, the inlet nozzle 104 of the first compartment being adjacent to the outlet nozzle 6 of the second compartment and the outlet nozzle 105 of the first compartment being adjacent to the inlet nozzle 6 of the second compartment.

The support structure 60 essentially comprises an elongated flat body 61 and a lower and an upper braces 62, 63 that extend at both ends of the body 61, from the same side thereof. The elongated body 61 has an overall rectangular shape. It is slightly longer and slightly narrower than the filter 100. The function of the braces 62, 63 is to mechanically and fluidly connect the filter 100 to the structure 60. Each brace 62/63 comprises an upper and a lower sockets having parallel axis that are designed to receive a pair of adjacent inlet/outlet nozzles (104/6 or 105/6) of the filter 100. The distance between the two braces 62, 63 corresponds to the distance between the two pairs of nozzles 104/6 and 105/6 of the filter 100 so that the nozzles can be engaged in the braces and the filter 100 secured to the structure 60.

The support structure 60 comprises a plurality of conduits defined therein as well as a first and a second pressure measurement chambers 7, 8.

A first conduit 64, extending through the lower brace 62 and the body 61, connects the upper socket of the lower brace 62 to an outlet nozzle 65 for a used liquid (e.g. blood ultrafiltrate, or used dialysis liquid or both) that is connected to the body 61 on the side thereof opposite the filter 100.

A second conduit 66, extending through the upper brace 63 and the body 61, connects the lower socket of the upper brace 63 to an inlet nozzle 67 for a fresh treatment liquid (e.g. a fresh dialysis liquid) that is connected to the body 61 on the side thereof opposite the filter 100.

A third conduit 68, extending through the body 61, has a first segment that connects a blood withdrawal tube 69 to an inlet 10 of the blood chamber of a first pressure measurement chamber 7 and a second segment that connects the outlet 11 of the blood chamber of the first pressure measurement chamber 7 to the first (upstream) end 18 of a pump hose 17. The air chamber of the first pressure measurement chamber 7 is delimited by a circular lid having a central port 12 for connection to a pressure sensor.

A fourth conduit 70, extending through the lower brace 62 and the body 61, connects the lower socket of the lower brace 62 to the second (downstream) end 16 of the pump hose 17. The third and fourth conduits 68, 70 are so defined within the body 60 that the pump hose 17 connected thereto forms a U shaped loop extending in the same plane as the flat body 61, and ready to engage the rotor of a peristaltic pump.

A fifth conduit 71, extending through the body 61, has a first segment that connects the outlet port 35 of the blood degassing device 30 to an inlet 10 of the blood chamber of a second pressure measurement chamber 8 and a second segment that connects the outlet 11 of the blood chamber of the second pressure measurement chamber 8 to a blood return tube 72. The air chamber of the second pressure measurement chamber 8 is delimited by a circular lid having a central port 12 for connection to a pressure sensor. Note that the central axis of the inlet and outlet nozzles 65, 67 and the central axis of the measurement ports 12 of the pressure measurement chambers 7, 8 extend in the same plane, are parallel, and are perpendicular to the elongated body 61 of the support structure 60.

A sixth conduit 73, extending through the body 61, connects an infusion tube 74 to the fourth conduit 70. The infusion tube 74 is therefore connected to the blood circuit upstream of the filter 100 and is intended for so-called pre-dilution infusion.

A seventh conduit 75, extending through the body 61, connects an infusion tube 76 to the fifth conduit 71. The infusion tube 76 is therefore connected to the blood circuit downstream of the filter 100 and is intended for so-called post-dilution infusion.

A eighth conduit 78, extending through the body 61, connects an anticoagulant tube 79 to the fourth conduit 70.

Figure 6:
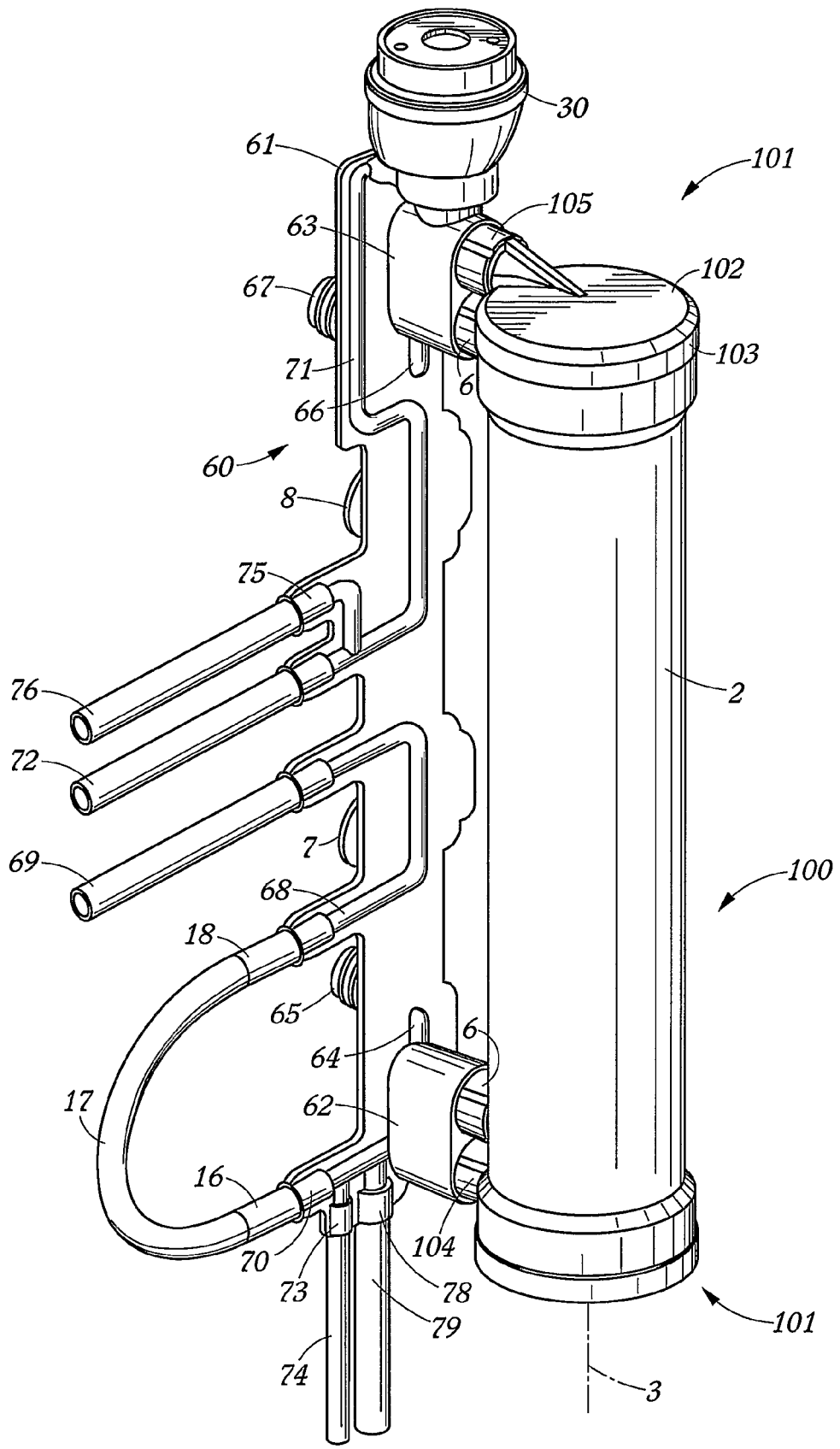
FIG. 6 is a perspective view of a second embodiment of the integrated blood treatment module according to the invention.
Figure 7:
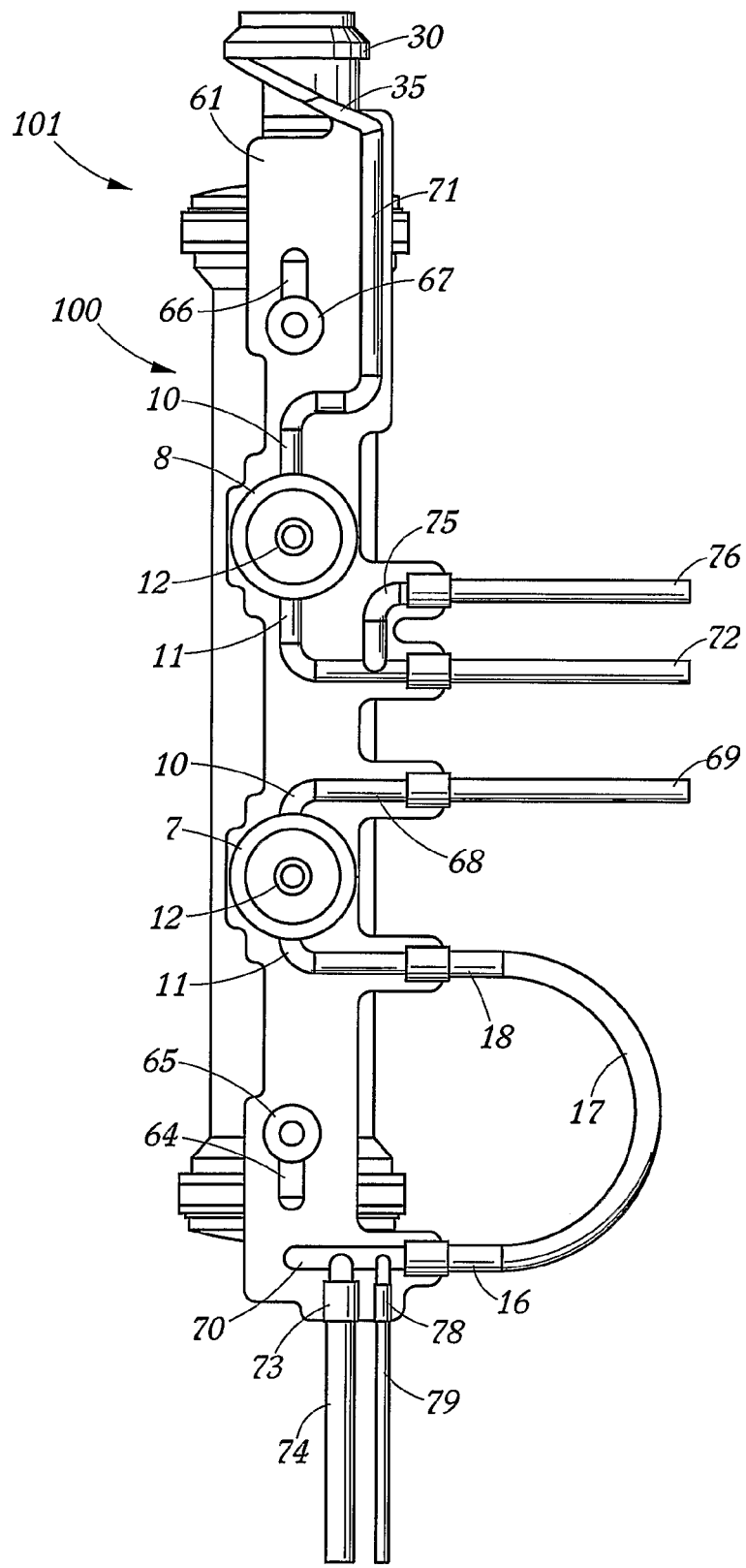
FIG. 7 is a rear view of a of the integrated blood treatment module of FIG. 6.
Figure 8:
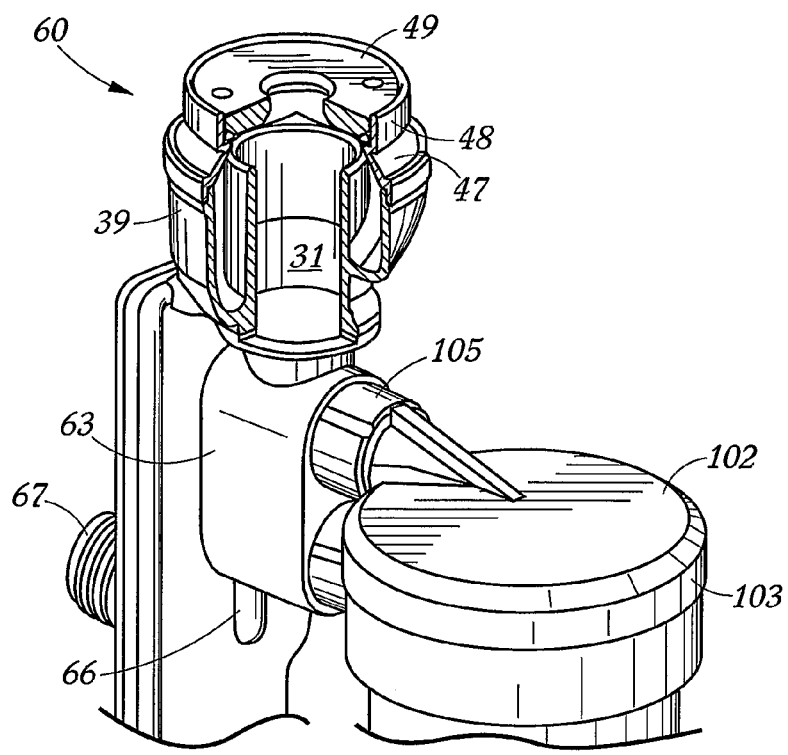
FIG. 8 is a perspective view, partially cut-away, of the upper portion of the integrated blood treatment module of FIG. 6.
Figure 9:
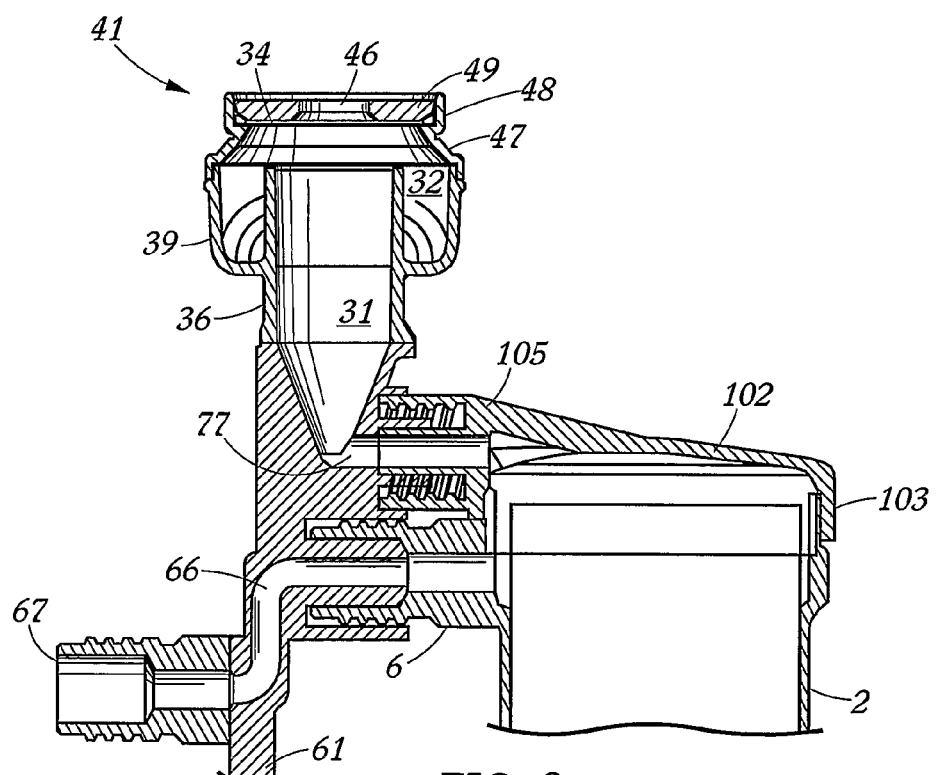
FIG. 9 is a cross-section view of the upper portion of the integrated blood treatment module of FIG. 6, along a plane that contains the longitudinal axis of the treatment device.

Except the inlet of the fifth conduit 71 and the inlet of the sixth and eighth conduits 73, 78, which open at the upper and lower side of the body 61 respectively (when the integrated blood treatment module is in an operational position), the inlet/outlet of the third, fourth, seventh conduits 68, 70, 75 and the outlet of the fifth conduit 71 open on the same side of the body 61. Note also that the two pressure measurement chambers 7, 8 are embedded in the body 61 between the inlet and outlet nozzles 65, 67 for the second compartment of the filter 100. Also since the third conduit 68 is embedded in the body 61 at a distance of both ends of the body 61 (i.e. of the filter 100), the loop formed by the pump hose 17 extends laterally with respect to the filter 100. It results from these various dispositions that the integrated blood treatment module of the FIGS. 6 and 7 is particularly compact.

The body 61 can be made in one piece by molding of a plastic material with the conduits defined therein. Only the membrane of the two pressure measurement chambers 7, 8 and the lid that delimit the air compartment thereof have to be manufactured as separate components and mounted later on the body 61.

The blood degassing device 30 is connected by a conduit 77 to the upper socket of the upper brace 63. As apparent in FIGS. 8 and 9, the blood degassing device 60 is the same as device represented in FIG. 5, save for the upstream part of its first chamber 31, that is conical with an increasing cross-section in the direction of flow.

Figure 10:
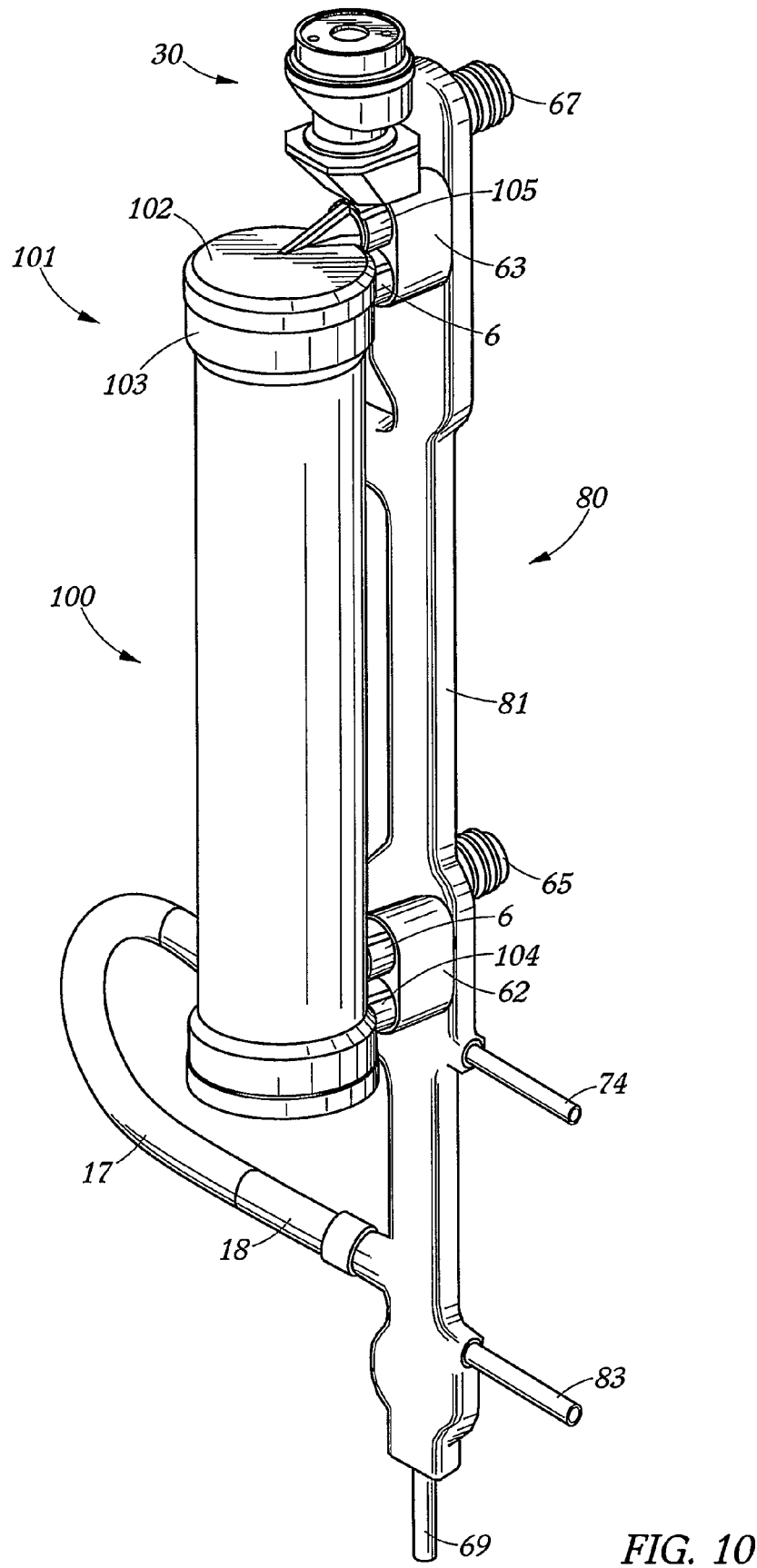
FIG. 10 is a perspective view of a third embodiment of the integrated blood treatment module according to the invention.
Figure 11:
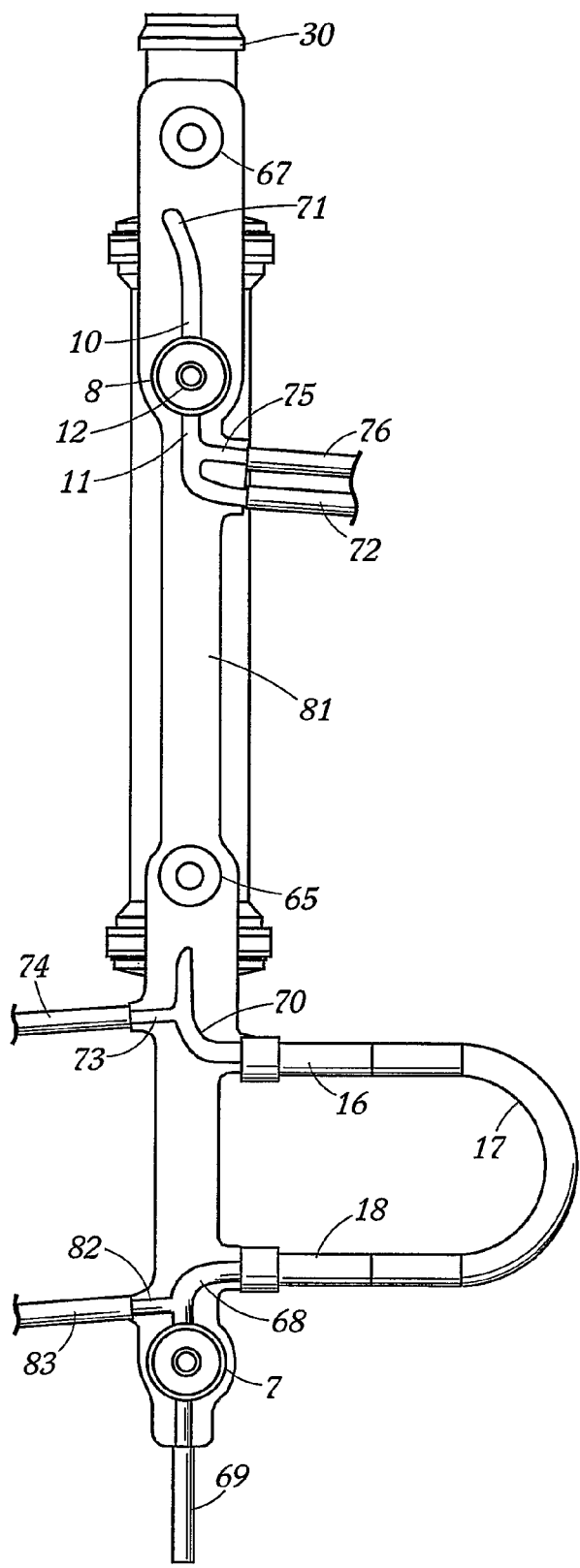
FIG. 11 is a rear view of a of the integrated blood treatment module of FIG. 10.

FIGS. 10 and 11 show a third embodiment of the integrated blood treatment module according to the invention. This integrated blood treatment module comprises a support structure 80 having a plurality of conduits defined therein, a filter 100 and a blood degassing device 30 that are secured to the structure 80.

This third embodiment essentially differs from the second embodiment by the shape of its support structure 80 and the location of the third conduit 68 and of the first pressure measurement chamber 7, which determine the position of the pump hose 17. The overall function of the blood treatment device and of its various components remains the same.

More specifically, the features that are specific to the integrated blood treatment module of FIGS. 10 and 11 are as follows:

The flat elongated body 81 is substantially longer than the filter 100 and its is secured to the filter so that a substantial portion thereof extends beyond the filter with respect to the lower end-cap 101 of the filter 100.

The third conduit 68 and the first pressure measurement chamber 7 are located in the lowest part of the body 81, whereas the fourth conduit 70 is adjacent to the lower end-cap of the filter. It results from this arrangement that the loop formed by the pump hose 17 extends laterally with respect to the longitudinal axis 3 of the filter, below the filter 100.

The inlet of the third conduit 68, which is connected to the blood withdrawal tube 69 opens on the lowest side of the elongated body 81.

A ninth conduit 82, extending through the body 81, connects an infusion tube 83 to the third conduit 68, upstream of the pump hose 17.

The inlet of the ninth conduit 82 opens on the side of the elongated body 81 opposite to the side thereof to which the pump hose 17 is connected.

The inlet of the sixth conduit 73, which is connected to the infusion tube 74, opens on the side of the elongated body 81 opposite to the side thereof to which the pump hose 17 is connected.

Figure 12:
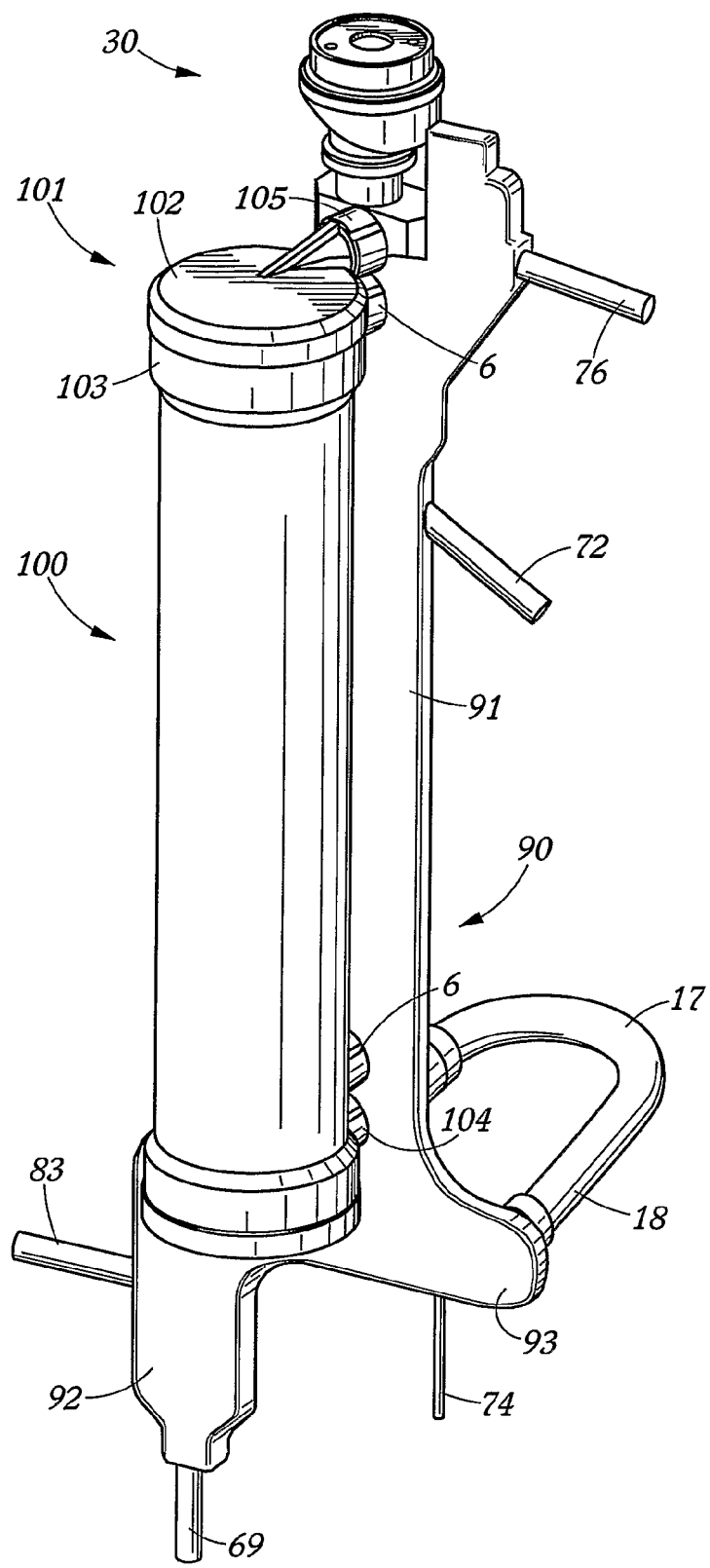
FIG. 12 is a perspective view of a fourth embodiment of the integrated blood treatment module according to the invention.
Figure 13:
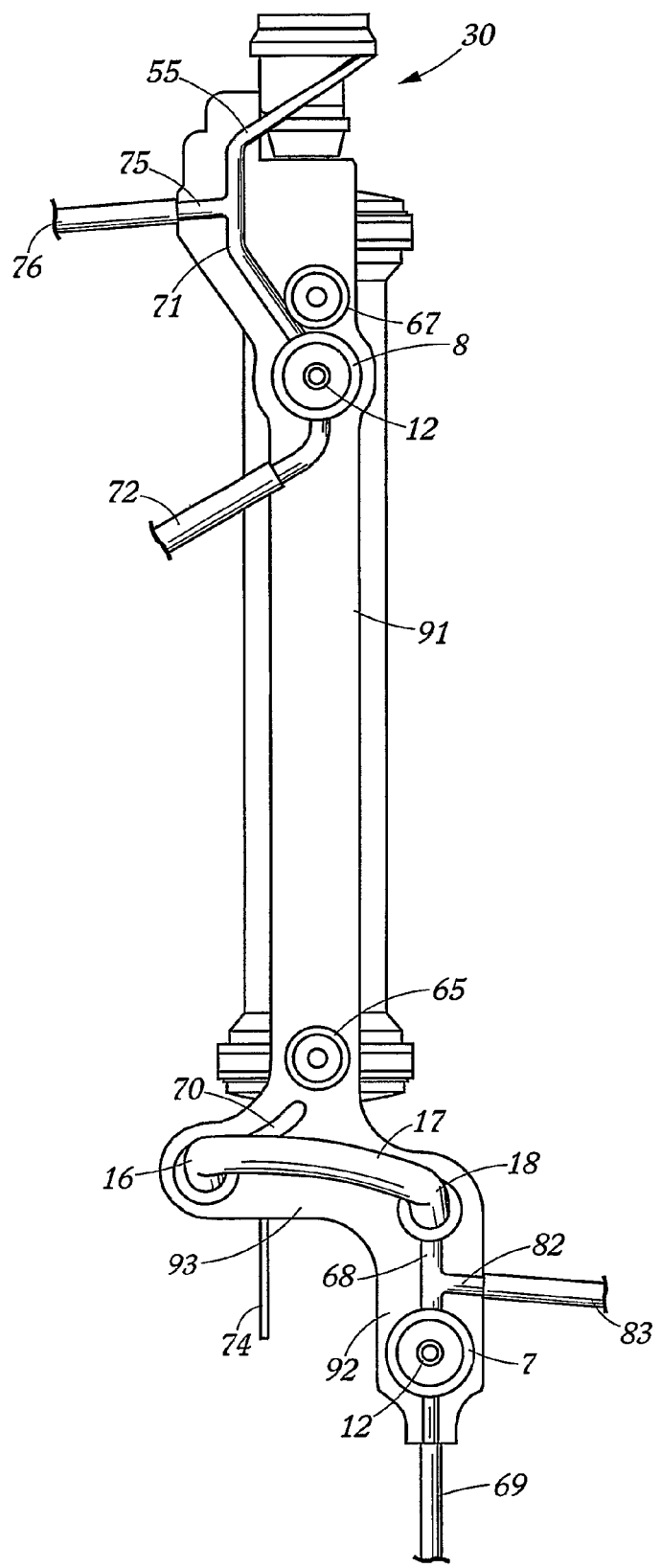
FIG. 13 is a rear view of a of the integrated blood treatment module of FIG. 12.

FIGS. 12 and 13 show a fourth embodiment of the integrated blood treatment module according to the invention. This integrated blood treatment module comprises a support structure 90 having a plurality of conduits defined therein, a filter 100 and a blood degassing device 30 that are secured to the structure 90.

This fourth embodiment essentially differs from the second embodiment by the shape of its support structure 90 and the location of the third conduit 68 and of the first pressure measurement chamber 7, which determines the position of the pump hose 17. The overall function of the blood treatment device and of its various components remains the same.

More specifically, the features that are specific to the integrated blood treatment module of FIGS. 12 and 13 are as follows:

The flat elongated body comprises a first long branch 91 and a second short branch 92, which are parallel, connected by a third transversal branch 93, the longitudinal axis of which is slightly inclined with respect to the longitudinal axes of the first and second branches 91, 92. The longitudinal axis of the three branches 91, 92, 93 are in the same plane. The first branch 91 has approximately the same length as the filter 100 and is connected by its lower end to the transversal branch 93, at the middle thereof. The third transversal branch 93 is slightly longer than the diameter of the loop of a U shaped pump hose 17 for a peristaltic pump adapted to pump blood. The second short branch 92 is connected by its upper end to the lower end of the third branch 93.

The third conduit 68 extends in the second branch 92 and in the third branch 93, along the longitudinal axis of the second branch 92, so that its outlet opens in the lower end of the transversal branch 93, on the face of the body 91, 92, 93 opposite the filter 100.

The fourth conduit 70 extends in the first branch 91 and in the third branch 93 so that its inlet opens in the upper end of the transversal branch 93, on the face of the body 91, 92, 93 opposite the filter 100.

The pump hose 17, which has a first (upstream) end 18 connected to the outlet of the third conduit 68 and a second (downstream) end 16 connected to the inlet of the fourth conduit 70, forms a loop that extends in a plane that is perpendicular to the plane containing the longitudinal axis of the three branches 91, 92, 93 of the body of the structure 90. Note that when the blood treatment module is held in its operative position, i.e. vertical, the inlet end 18 of the pump hose 17 is lower than its outlet end 16. The purpose of this disposition is to help degas the pump hose during the priming of the blood treatment module.

The inlet of the third conduit 68, which is connected to the blood withdrawal tube 69 opens on the lowest side of the elongated body 91, 92, 93.

An ninth conduit 82, extending through the short branch 92 of the body, connects an infusion tube 83 to the third conduit 68, upstream of the pump hose 17.

The seventh conduit 75 is connected to the fifth conduit 71 upstream of the second pressure measurement chamber 8.

The inlet of the ninth conduit 83 opens on one lateral side of the elongated body 91, 92, 93, whereas the inlet of the seventh conduit 75 and the outlet of the fifth conduit 71 opens on the other lateral side of the elongated body 91, 92, 93.

The various embodiments of the invention described above are only to exemplify the invention. The scope of the invention is therefore not limited to any of them.

The invention claimed is:

1. An integrated blood treatment module, comprising:
   a blood treatment device having:
      a housing having a longitudinal axis,
      a first end-cap closing a first end of the housing, the first end-cap having a blood inlet port,
      a second end-cap closing a second end of the housing;
   a pump hose for a peristaltic pump, wherein the pump hose has a first end fluidly connected to the housing and a second end that is fluidly connected to the blood inlet port; and
   a degassing device connected to the second end-cap having:
      a first chamber having an inlet for receiving a liquid flowing into the second end-cap, and
      a second chamber having an opening closed by a hydrophobic membrane and an outlet for discharging the liquid,
      wherein the outlet of the second chamber is above the inlet of the first chamber,
      wherein the first chamber has a downstream portion that partially extends within the second chamber and communicates therewith by a passageway,
      wherein the second chamber has a downstream portion that extends below the passageway, and
      wherein the downstream portion of the second chamber extends completely around an upper region of the first chamber and only partially around a lower region of the first chamber.

2. An integrated blood treatment module according to claim 1, further comprising:
   a first pressure measurement chamber that is secured to the blood treatment device and is connected to the first end of the pump hose, the first pressure measurement chamber having a first pressure measurement port for connection to a first pressure sensor, and the first pressure measurement port having a central axis that is parallel to a central axis of at least one access port of the housing.

3. An integrated blood treatment module according to claim 2, further comprising:
   a second pressure measurement chamber that is secured to the blood treatment device and is connected to the outlet port of the degassing device, the second pressure measurement chamber having a second pressure measurement port for connection to a second pressure sensor, the second pressure measurement port having a central axis that is parallel to a central axis of at least one access port of the housing.

4. An integrated blood treatment module according to claim 3, further comprising: a third pressure measurement chamber that is secured to the blood treatment device and is connected to the second end of the pump hose, the third pressure measurement chamber having a third pressure measurement port for connection to a third pressure sensor, the third pressure measurement port having a central axis that is parallel to a central axis of at least one access port of the housing.

5. An integrated blood treatment module according to claim 1, further comprising:
   a support structure having a plurality of conduits defined therein, the blood treatment device being secured to the support structure.

6. An integrated blood treatment module according to claim 5, wherein the support structure comprises a first conduit having a first end connected to a first access port of the housing, and a second end comprised of an outlet nozzle for a waste liquid.

7. An integrated blood treatment module according to claim 5, wherein the support structure comprises a second conduit having a first end connected to a second access port of the housing, and a second end comprised of an inlet nozzle for a dialysis liquid.

8. An integrated blood treatment module according to claim 5, wherein the support structure comprises:
   a third conduit having an inlet for connection to a blood withdrawal tube, and an outlet connected to the first end of the pump hose; and
   a fourth conduit having an inlet connected to the second end of the pump hose, and an outlet connected to the blood inlet port of the first end-cap.

9. An integrated blood treatment module according to claim 8, wherein the support structure comprises a sixth conduit having a first end connected to the fourth conduit and a second end for connection to a pre-dilution infusion tube.

10. An integrated blood treatment module according to claim 8, further comprising:
    a first pressure measurement chamber defined within the support structure and connected to the third conduit for measuring a pressure upstream of the pump hose.

11. An integrated blood treatment module according to claim 8, wherein the outlet of the third conduit and the inlet of the fourth conduit are arranged with respect to each other so that the pump hose forms a loop that extends in a plane substantially parallel to the longitudinal axis of the housing.

12. An integrated blood treatment module according to claim 11, wherein the outlet of the third conduit is located between the two end-caps and the loop formed by the pump hose extends laterally with respect to the housing of the blood treatment device.

13. An integrated blood treatment module according to claim 11, wherein the outlet of the third conduit is located along the longitudinal axis of the housing beyond the first end-cap, and the loop formed by the pump hose is offset along the longitudinal axis of the housing with respect to the housing of the blood treatment device.

14. An integrated blood treatment module according to of claim 8, wherein the outlet of the third conduit and the inlet of the fourth conduit are arranged with respect to each other so that the pump hose forms a loop that extends in a plane inclined with respect to a plane substantially perpendicular to the longitudinal axis of the housing.

15. An integrated blood treatment module according to claim 5, wherein the support structure comprises a fifth conduit having an inlet connected to the outlet port of the blood degassing device, and an outlet for connection to a blood return tube.

16. An integrated blood treatment module according to claim 15, wherein the support structure comprises a seventh conduit having a first end connected to the fifth conduit and a second end for connection to a post-dilution infusion tube.

17. An integrated blood treatment module according to claim 15, further comprising:
 a second pressure measurement chamber defined within the support structure and connected to the fifth conduit for measuring a pressure downstream of the blood degassing device.

18. An integrated blood treatment module according to claim 17, further comprising,
 a first pressure measurement chamber defined within the support structure and connected to the third conduit for measuring a pressure upstream of the pump hose,
 wherein the first pressure measurement chamber has a port for connection to a first pressure sensor, the second pressure measurement chamber has a port for connection to a second pressure sensor, and
 wherein the inlet nozzle, the outlet nozzle, the port of the first pressure measuring chamber and the port of the second measuring chamber have respective central axes that are substantially parallel.

19. An integrated blood treatment module according to claim 18, wherein the respective central axes of the inlet nozzle, the outlet nozzle, the port of the first pressure measuring chambers and the port of the second measuring chamber are substantially perpendicular to the longitudinal axis of the housing.

20. An integrated blood treatment module according to claim 1, wherein the downstream portion of the second chamber has a lateral wall that surrounds a longitudinal axis of the degassing device and a bottom wall that is inclined with respect to the longitudinal axis of the degassing device.

21. An integrated blood treatment module according to claim 20, wherein the downstream portion of the first chamber has a lateral wall that is concentric to the lateral wall of the second chamber.

22. An integrated blood treatment module according to claim 21, wherein the lateral wall of the downstream portion of the first chamber and the lateral wall of the downstream portion of the second chamber are substantially cylindrical.

23. An integrated blood treatment module according to claim 1, wherein the downstream portion of the first chamber has a cross-section that is substantially the same as a cross-section of the passageway between the first and the second chamber chambers.

24. An integrated blood treatment module according to claim 1, wherein the first chamber comprises an upstream portion having a decreasing cross section.

25. An integrated blood treatment module according to claim 1, wherein the second chamber comprises an upstream portion extending above the passageway that has a decreasing cross-section, with a larger cross-section that is substantially level with the passageway and a smaller cross-section that is substantially level with the hydrophobic membrane.

26. An integrated blood treatment module according to claim 25, wherein the upstream portion of the second chamber is substantially frusto-conical.

27. An integrated blood treatment module according to claim 1, wherein the outlet port opens in the downstream portion of the second chamber at a location furthest to the passageway.

28. An integrated blood treatment module according to claim 1, wherein the first chamber of the degassing device has a downstream portion having a cross-section selected with respect to a maximal flow rate of a liquid in the module so that a velocity of the liquid in the downstream portion of the first chamber is less than a predetermined velocity.

29. An integrated blood treatment module according to claim 28, wherein the cross-section of the downstream portion of the first chamber is selected with respect to the maximal flow rate of the liquid of about 500 ml/min in the module so that the velocity of the liquid in the downstream portion of the first chamber is less than about 3 m/min.

30. An integrated blood treatment module according to claim 1, wherein the cross-section of the second chamber of the degassing device at a level of the passageway is selected so that a ratio of a velocity of a liquid within a downstream portion of the first chamber to a velocity of the liquid within the second chamber at the level of the passageway is more than a determined value.

31. An integrated blood treatment module according to claim 30, wherein the cross-section of the second chamber of the degassing device at the level of the passageway is selected so that the ratio of the velocity of the liquid within the downstream portion of the first chamber to the velocity of the liquid within the second chamber at the level of the passageway is at least about 2.

32. An integrated blood treatment module according to claim 1, wherein the downstream portion of the second chamber forms an overflow for a fluid flowing from the first chamber into the second chamber.

33. An integrated blood treatment module according to claim 1, wherein the first chamber, the second chambers and the passageway therebetween are arranged with respect to each other so that a flow pattern of a liquid flowing from the first chamber through the second chamber and to the outlet comprises a component that is tangential to the membrane.

34. An integrated blood treatment module according to claim 33, wherein a flow pattern of a liquid flowing from the first chamber through the second chamber and to the outlet comprises an umbrella-like component.

35. An integrated blood treatment module according to claim 1, wherein the first chamber, the second chamber, and the passageway therebetween are arranged with respect to each other so that a flow of liquid flowing from the first chamber through the second chamber and to the outlet keeps gas bubbles in motion along an inner surface of the hydrophobic membrane.

36. An integrated blood treatment module according to claim 1, further comprising:
 a protective member for protecting the hydrophobic membrane against external blows and for limiting a deformation of the hydrophobic membrane when a pressure of the liquid within the degassing device exceeds a limit.

37. An integrated blood treatment module according to claim 1, wherein the hydrophobic membrane is arranged in a plane substantially perpendicular to a longitudinal axis of the degassing device.

38. An integrated blood treatment module according to claim 1, wherein the blood treatment device is a hemodialyzer, a hemofilter or a plasmafilter.

39. An integrated blood treatment module, comprising:
a blood treatment device having:
  a housing having a longitudinal axis,
  a first end-cap closing a first end of the housing, the first end-cap having a blood inlet port, and
  a second end-cap closing a second end of the housing;
a pump hose for a peristaltic pump, wherein the pump hose has a first end that is fluidly connected to the housing and a second end that is fluidly connected to the blood inlet port;
a degassing device connected to the second end-cap having:
  a first chamber having an inlet for receiving a liquid flowing into the second end-cap, and
  a second chamber having an opening closed by a hydrophobic membrane and an outlet for discharging the liquid,
  wherein the outlet of the second chamber is above the inlet of the first chamber,
  wherein the first chamber has a downstream portion that partially extends within the second chamber and communicates therewith by a passageway, and
  wherein the second chamber has a downstream portion that extends below the passageway, and
  wherein the downstream portion of the second chamber extends around an upper region of the downstream portion of the first chamber to a greater degree than around a lower region of the downstream portion of the first chamber; and
a support structure having a plurality of conduits defined therein, the blood treatment device being secured to the support structure.

40. An integrated blood treatment modules comprising:
a blood treatment device having:
  a housing having a longitudinal axis,
  a first end-cap closing a first end of the housing, the first end-cap having a blood inlet port, and
  a second end-cap closing a second end of the housing;
a pump hose for a peristaltic pump, wherein the pump hose has a first end that is fluidly connected to the housing and a second end that is fluidly connected to the blood inlet;
a degassing device connected to the second end-cap having:
  a first chamber having:
    an inlet for receiving a liquid flowing into the second end-cap, and
  a second chamber having an opening closed by a hydrophobic membrane and an outlet for discharging the liquid,
  wherein the outlet of the second chamber is above the inlet of the first chamber,
  wherein the first chamber has a downstream portion that partially extends within the second chamber and communicates therewith by a passageway,
  wherein the second chamber has a downstream portion that extends below the passageway and asymmetrically surrounds the downstream portion of the first chamber, and
  wherein the downstream portion of the second chamber extends around an upper region of the downstream portion of the first chamber to a greater degree than around a lower region of the downstream portion of the first chamber; and
a support structure having a plurality of conduits defined therein, wherein the blood treatment device is secured to the support structure, and the support structure comprises:
  a third conduit having an inlet for connection to a blood withdrawal tube, and an outlet connected to the first end of the pump hose; and
  a fourth conduit having an inlet connected to the second end of the pump hose, and an outlet connected to the blood inlet port of the first end-cap.

41. An integrated blood treatment module, comprising:
a blood treatment device having:
  a housing having a longitudinal axis,
  a first end-cap closing a first end of the housing, the first end-cap having a blood inlet port, and
  a second end-cap closing a second end of the housing;
a pump hose for a peristaltic pump, wherein the pump hose has a first end that is fluidly connected to the housing and a second end that is fluidly connected to the blood inlet;
a degassing device connected to the second end-cap having:
  a first chamber having an inlet for receiving a liquid flowing into the second end-cap, and
  a second chamber having an opening closed by a hydrophobic membrane and an outlet for discharging the liquid,
  wherein the outlet of the second chamber is above the inlet of the first chamber,
  wherein the first chamber has a downstream portion that partially extends within the second chamber and communicates therewith by a passageway,
  wherein the second chamber has a downstream portion that extends below the passageway, and
  wherein the degree to which the downstream portion of the second chamber extends around the downstream portion of the first chamber decreases in a downstream direction of flow through the second chamber; and
a support structure having a plurality of conduits defined therein, wherein the blood treatment device is secured to the support structure, and the support structure comprises:
  a third conduit having an inlet for connection to a blood withdrawal tube, and an outlet connected to the first end of the pump hose; and
  a fourth conduit having an inlet connected to the second end of the pump hose, and an outlet connected to the blood inlet port of the first end-cap,
  wherein the outlet of the third conduit and the inlet of the fourth conduit are arranged with respect to each other so that the pump hose forms a loop that extends in a plane substantially parallel to the longitudinal axis of the housing.

42. An integrated blood treatment module, comprising:
a blood treatment device having:
  a housing having a longitudinal axis,
  a first end-cap closing a first end of the housing, the first end-cap having a blood inlet port, and
  a second end-cap closing a second end of the housing;
a pump hose for a peristaltic pump, wherein the pump hose has a first end that is fluidly connected to the housing and a second end that is fluidly connected to the blood inlet port;
a degassing device connected to the second end-cap having:
  a first chamber having an inlet for receiving a liquid flowing into the second end-cap, and
  a second chamber having an opening closed by a hydrophobic membrane and an outlet for discharging the liquid, wherein the outlet of the second chamber is above the inlet of the first chamber, wherein the first chamber has a downstream portion that partially extends within the second chamber and communicates therewith by a passageway, wherein the second chamber has a downstream portion that extends below the passageway, and wherein the degree to which the downstream portion of the second chamber extends around the downstream portion of the first chamber gradually decreases in a downstream direction of flow through the second chamber; and a support structure having a plurality of conduits defined therein, wherein the blood treatment device is secured to the support structure, and the support structure comprises:
  a third conduit having an inlet for connection to a blood withdrawal tube, and an outlet connected to the first end of the pump hose; and
  a fourth conduit having an inlet connected to the second end of the pump hose, and an outlet connected to the blood inlet port of the first end-cap,
  wherein the outlet of the third conduit and the inlet of the fourth conduit are arranged with respect to each.

43. An integrated blood treatment module, comprising:
a blood treatment device having:
  a housing having a longitudinal axis,
  a first end-cap closing a first end of the housing, the first end-cap having a blood inlet port, and
  a second end-cap closing a second end of the housing;
a pump hose for a peristaltic pump, wherein the pump hose has a first end that is fluidly connected to the housing and a second end that is fluidly connected to the blood inlet port; and
a degassing device connected to the second end-cap having:
  a first chamber having an inlet for receiving a liquid flowing into the second end-cap, and
  a second chamber having an opening closed by a hydrophobic membrane and an outlet for discharging the liquid,
  wherein the outlet of the second chamber is above the inlet of the first chamber,
  wherein the first chamber has a downstream portion that partially extends within the second chamber and communicates therewith by a passageway,
  wherein the second chamber has a downstream portion that extends below the passageway, and
  wherein the degree to which the downstream portion of the second chamber extends around the downstream portion of the first chamber reduces along a downstream direction of flow through the second chamber, and
  wherein the downstream portion of the second chamber has a lateral wall that surrounds a longitudinal axis of the degassing device and a bottom wall that is inclined with respect to a longitudinal axis of the degassing device.

44. An integrated blood treatment module, comprising:
a blood treatment device having:
  a housing having a longitudinal axis,
  a first end-cap closing a first end of the housing, the first end-cap having a blood inlet port, and
  a second end-cap closing a second end of the housing;
a pump hose for a peristaltic pump, wherein the pump hose has a first end that is fluidly connected to the housing and a second end that is fluidly connected to the blood inlet port; and
a degassing device connected to the second end-cap having:
  a first chamber having an inlet for receiving a liquid flowing into the second end-cap, and
  a second chamber having an opening closed by a hydrophobic membrane and an outlet for discharging the liquid,
  wherein the outlet of the second chamber is above the inlet of the first chamber,
  wherein the first chamber has a downstream portion that partially extends within the second chamber and communicates therewith by a passageway,
  wherein the second chamber has a downstream portion that extends below the passageway,
  wherein the degree to which the downstream portion of the second chamber extends around the downstream portion of the first chamber gradually reduces along a downstream direction of flow through the second chamber, and
  an upstream portion of the second chamber extending above the passageway that has a decreasing cross-section, with a larger cross-section that is substantially level with the passageway and a smaller cross-section that is substantially level with the hydrophobic membrane.

45. An integrated blood treatment module, comprising:
a blood treatment device having:
  a housing having a longitudinal axis,
  a first end-cap closing a first end of the housing, the first end-cap having a blood inlet port, and
  a second end-cap closing a second end of the housing;
a pump hose for a peristaltic pump, wherein the pump hose has a first end that is connected to the housing to provide fluid communication between the first end and the housing, and a second end that is connected to provide fluid communication to the blood inlet port; and
a degassing device connected to the second end-cap having:
  a first chamber having an inlet for receiving a liquid flowing into the second end-cap,
  a second chamber having an opening closed by a hydrophobic membrane and an outlet for discharging the liquid,
  wherein the outlet of the second chamber is above the inlet of the first chamber,
  wherein the degree to which the second chamber extends around the first chamber gradually reduces in a downstream direction of flow through the second chamber, and
  wherein the first chamber has a downstream portion that partially extends within the second chamber, communicates therewith by a passageway, and has a cross-section selected with respect to a maximal flow rate of the liquid in the module so that a velocity of the liquid in the downstream portion of the first chamber is less than a predetermined velocity.

46. An integrated blood treatment module, comprising:
a blood treatment device having:
  a housing having a longitudinal axis,
  a first end-cap closing a first end of the housing, the first end-cap having a blood inlet port, and
  a second end-cap closing a second end of the housing;

a pump hose for a peristaltic pump, wherein the pump hose has a first end that is connected the housing to provide fluid communication between the first end of the pump hose and the housing, and a second end that is connected to provide fluid communication between the second end of the pump hose and the blood inlet port; and a degassing device connected to the second end-cap having:
- a first chamber having an inlet for receiving a liquid flowing into the second end-cap, and
- a second chamber having an opening closed by a hydrophobic membrane and an outlet for discharging the liquid,
- wherein the outlet of the second chamber is above the inlet of the first chamber,
- wherein the first chamber has a downstream portion that partially extends within the second chamber and communicates therewith by a passageway,
- wherein the degree to which the second chamber extends around the downstream portion of the first chamber decreases in a downward direction, and
- wherein the cross-section of the second chamber of the degassing device at a level of the passageway is selected so that a ratio of a velocity of the liquid within a downstream portion of the first chamber to a velocity of the liquid within the second chamber at the level of the passageway is more than a determined value.

47. An integrated blood treatment modules comprising:
a blood treatment device having:
- a housing having a longitudinal axis,
- a first end-cap closing a first end of the housing, the first end-cap having a blood inlet port, and
- a second end-cap closing a second end of the housing;

a pump hose for a peristaltic pump, wherein the pump hose has a first end that is connected to the housing to provide fluid communication between the first end of the pump hose and the housing, and a second end that is connected to provide fluid communication between the second end of the pump hose and the blood inlet port; and a degassing device connected to the second end-cap having:
- a first chamber having an inlet for receiving a liquid flowing into the second end-cap, and
- a second chamber having an opening closed by a hydrophobic membrane and an outlet for discharging the liquid,
- wherein the outlet of the second chamber is above the inlet of the first chamber,
- wherein the first chamber has a downstream portion that partially extends within the second chamber and communicates therewith by a passageway,
- wherein the degree to which the first chamber is encircled by the second chamber reduces in a downstream direction of flow through the second chamber, and
- wherein the first chamber, the second chamber, and the passageway therebetween are arranged with respect to each other so that a flow pattern of the liquid flowing from the first chamber through the second chamber and to the outlet comprises a component that is tangential to the hydrophobic membrane.

48. An integrated blood treatment module, comprising:
a blood treatment device having:
- a housing having a longitudinal axis;
- a first end-cap closing a first end of the housing, the first end-cap having a blood inlet port, and
- a second end-cap closing a second end of the housing;

a pump hose for a peristaltic pump, wherein the pump hose has a first end that is connected to the housing to provide fluid communication between the first end of the pump hose and the housing, and a second end that is connected to provide fluid communication between the pump hose and the blood inlet port; and a degassing device connected to the second end-cap having:
- a first chamber having an inlet for receiving a liquid flowing into the second end-cap, and
- a second chamber having an opening closed by a hydrophobic membrane and an outlet for discharging the liquid,
- wherein the outlet of the second chamber is above the inlet of the first chamber,
- wherein the first chamber has a downstream portion that partially extends within the second chamber and communicates therewith by a passageway,
- wherein the degree to which the second chamber extends around the downstream portion of the first chamber gradually reduces in a downstream direction of the flow through the second chamber, and
- wherein the first chamber, the second chambers and the passageway therebetween are arranged with respect to each other so that a flow of the liquid flowing from the first chamber through the second chamber and to the outlet keeps gas bubbles in motion along an inner surface of the hydrophobic membrane.

49. The integrated blood treatment module in claim 1 wherein the downstream portion of the second chamber asymmetrically surrounds at least partially the downstream portion of the first chamber.

* * * * *